US010969802B2

(12) United States Patent
Shah

(10) Patent No.: US 10,969,802 B2
(45) Date of Patent: Apr. 6, 2021

(54) SOLENOID OPERATED UNIT FOR DETECTING AND REMOVING UNDESIRED FLUID WITH DIAGNOSTIC METERING

(71) Applicant: ROTEX AUTOMATION LIMITED, Gujarat (IN)

(72) Inventor: Nirav R Shah, Gujarat (IN)

(73) Assignee: Rotex Automation Limited, Gujarat (IN)

(*) Notice: Subject to any disclaimer, the term of this patent is extended or adjusted under 35 U.S.C. 154(b) by 250 days.

(21) Appl. No.: 16/149,164

(22) Filed: Oct. 2, 2018

(65) Prior Publication Data
US 2019/0101937 A1 Apr. 4, 2019

(30) Foreign Application Priority Data
Oct. 3, 2017 (IN) .......................... IN201721034988

(51) Int. Cl.
| | |
|---|---|
| *G05D 7/06* | (2006.01) |
| *F04B 17/04* | (2006.01) |
| *G01N 33/28* | (2006.01) |
| *G01F 11/02* | (2006.01) |
| *B01D 17/02* | (2006.01) |
| *B01D 17/12* | (2006.01) |

(Continued)

(52) U.S. Cl.
CPC ....... *G05D 7/0676* (2013.01); *B01D 17/0214* (2013.01); *B01D 17/12* (2013.01); *F02M 37/24* (2019.01); *F02M 37/28* (2019.01); *F04B 17/04* (2013.01); *F04B 17/044* (2013.01); *G01F 11/021* (2013.01); *G01N 33/2847* (2013.01)

(58) Field of Classification Search
CPC .. B01D 17/0214; B01D 17/12; B01D 36/005; B01D 36/006; F02M 37/24; F02M 37/26; F02M 37/28; F04B 17/04; F04B 17/044; G01F 11/021; G01N 33/2847; G05D 7/0676

See application file for complete search history.

(56) References Cited

U.S. PATENT DOCUMENTS

| | | | | |
|---|---|---|---|---|
| 5,758,862 A | * | 6/1998 | Sturman | ............... F04B 43/067 |
| | | | | 251/25 |
| 6,783,665 B1 | * | 8/2004 | Girondi | ................ B01D 35/143 |
| | | | | 210/86 |

(Continued)

FOREIGN PATENT DOCUMENTS

| | | | | |
|---|---|---|---|---|
| DE | 3701259 A1 | * | 7/1987 | ........... B01D 36/006 |
| GB | 2065336 A | * | 6/1981 | ............. C10G 33/08 |

*Primary Examiner* — Terry K Cecil

(57) ABSTRACT

A solenoid operated unit (100) for detecting and removing an undesired fluid (6) from a desired fluid (5) with diagnostic metering, comprises a unified solenoid operated pump and valve unit (70), a drainage path (40), an electrical detection system (60), a mecha-electro-magnetic detection system (80) and a junction box (190) interacting with an electronic control unit (90) comprising a PWM generator. A plunger (50) moves from up to down, a sweeping volume (28) with a cycle of a PWM electricity wave, while moving down the plunger (50) creates a negative pressure in a sweeping volume (28) and while moving up a positive pressure gets created in the sweeping volume (28) and a negative pressure gets created at a rear end (30) of a unified chamber (26), an air reliever (180) is provided for breathing.

33 Claims, 28 Drawing Sheets

(51) Int. Cl.
 *F02M 37/24* (2019.01)
 *F02M 37/28* (2019.01)

(56) References Cited

U.S. PATENT DOCUMENTS

| | | | | |
|---|---|---|---|---|
| 8,409,446 B2* | 4/2013 | Abdalla | ............... | B01D 36/006 |
| | | | | 210/744 |
| 2010/0313980 A1* | 12/2010 | Shimizu | .................. | F04B 49/22 |
| | | | | 137/625.64 |
| 2018/0209387 A1* | 7/2018 | Rajagopalan | ........ | B01D 36/006 |

* cited by examiner

SOLENOID OPERATED UNIT FOR DETECTING AND REMOVING UNDESIRED FLUID WITH DIAGNOSTIC METERING

The following specification particularly describes the invention and the manner in which it is to be performed.

CLAIM OF PRIORITY

This application claims priority from Indian patent application number 201721034988 filed on Oct. 3, 2017 titled "A SOLENOID OPERATED UNIT FOR DETECTING AND REMOVING UNDESIRED FLUID".

FIELD OF INVENTION

The present invention relates to detection and separation of two immiscible liquids from each other and particularly to detection and separation of a liquid which has relatively higher density and conductivity. More particularly the invention relates to detection of such liquid electrically as well as electromagnetically and removing such liquid without atmospheric air replacing it.

BACKGROUND

Undesirable presence of one liquid in another is common. The background here focuses on those liquids which are immiscible with respect to each other. Further, only those liquids are in purviews which have different densities or specific gravities with respect to each other. A commonly occurring situation fitting such boundary conditions is water which could be present in different kinds of fluids like diesel, gasoline, lubricants, et cetera. Undesirable liquids, like water, can cause severe performance problems with the equipment, like engine. Water can cause the fuel injector tips to explode, resulting in expensive repairs. Slugs of water in the fuel can cause sudden cooling in the engine and may result in shortened engine life. Excessive water can reduce the lubricating qualities of the fuel and cause injector seizure and contingent engine damage. In addition, fungus and bacteria live in water. As a result, diesel fuel needs to be filtered essentially before injecting the diesel fuel into the engine. The problems that can be caused due to contaminants and water can be a significant matter of concern. When water encumbered diesel fuel is run through a fuel system and engine, the presence of free water could result the fuel system to malfunction enormously due to rust, corrosion, deposits, etc. all of which affect the life of the machine. Undesired liquids therefore need to be detected, separated and removed. Such removal is generally termed as bleeding or draining.

Designs are available that detect undesired fluid by making virtue of difference in density and have arrangement to harness density difference. U.S. Pat. No. 8,409,446B2 discloses an automatic draining system that includes a floating valve having a density less than a first fluid and greater than a second fluid.

In a system when water fuel separator is installed before primary pump, the system or water fuel separator always remains under vacuum or atmospheric pressure condition. In such challenging environment, draining the undesirable fluid becomes challenge as such draining either needs to allow atmospheric air to enter fuel system to replace the drained liquid volume or needs to have pump to suck the undesirable liquid. In the former case there are two potential hazards. Firstly, it may allow atmospheric air to go to fuel system and make the engine stall or jerk. Secondly, atmospheric air may carry along with it dust particles which may contaminate clean fuel and may risk injector functioning.

There are auto drain valves which drain such liquids but at the cost of allowing air to enter the system and de-aeration system may have to be provided additionally to counteract the same. Also in the event that the valve gets stuck while it is open, then there is no provision which may prevent such air leaking into the system.

Also there are motor based pump solutions but such solutions are bulky and cannot control precisely the amount of undesirable fluid getting bled and thus have higher chance of draining desirable fluid which in case of Diesel or fuels can be a safety hazard. Priming of such pumps may be a bottleneck and initial vacuum generation may be another concern.

There are disclosed solenoid based pumps. U.S. Pat. No. 5,758,862A discloses a flow control valve that has a solenoid operated pump that moves a poppet between an open and a closed position. Patent application US2010/0313980A1 discloses a solenoid valve functioning as electromagnetic pump.

Most devices lack redundancy and diagnostics and inefficient operation of such devices in terms of separation of undesired fluid results into rough performance of multicylinder engines and the flawed device remains unnoticed until next major overhaul.

Our invention effectively bridges the gap in current products deployed for detection and removal of undesired fluid, particularly detection and removal of water from diesel.

OBJECTIVE OF INVENTION

The objective is to invent a solenoid operated unit for detecting and removing immiscible liquid from another fluid of lower specific gravity and lower electrical conductivity.

The objective is to invent a device for detecting and removing immiscible liquid from another fluid of lower specific gravity and lower electrical conductivity placed in a chamber not having access to atmospheric pressure.

Yet another objective is to prevent air from entering the chamber while draining the undesirable liquid.

Yet another objective is to have redundancy such that desired fluid is not inadvertently removed due to malfunctioning.

Yet another objective is to invent a solenoid operated pump having redundancy in such a way that desired fluid is not inadvertently removed and atmospheric air is not added into the upstream due to malfunctioning.

Yet another objective is to detect immiscible liquid from another liquid of lower specific gravity redundantly by two independent detection methods.

Yet another objective is to detect immiscible liquid from another liquid of lower specific gravity redundantly by an analogue and a discrete electrical and or electromagnetic method precisely.

Yet another objective is to handle undesirable fluid contaminated with debris and dirt.

Yet another objective is to remove the undesired fluid when either of the independent detection methods activates.

Yet another objective is to remove the undesired fluid only when both of the independent detection methods activate.

Yet another objective is to have integrated connector inbuilt into solenoid valve connected WIF+Reed sensor and solenoid electrically.

Yet another objective is to design a pump with Valve function integrated and thus providing robust design which can work in higher vibration levels and also can withstand higher impulse pressures at the inlet side.

Yet another objective is to run the pump at higher duty cycle without excessive linear and or transversal wear.

Yet another objective is to design an integrated solenoid pump with valve action.

Yet another objective is to diagnose and predict failure.

Yet another objective is to diagnose and predict failure by metering.

SUMMARY

Present invention is a solenoid operated unit for detecting and removing an undesired fluid from a desired fluid with diagnostic metering. The desired fluid may be petrol or diesel. The solenoid operated unit comprises a unified solenoid operated pump and valve unit, which further comprises a combination housing having a first housing and a second housing, a solenoid coil circuit having an electromagnetic circuit integrated with a fluid circuit, and a pump-valve assembly having a unified chamber having a first liner and a second liner, a plunger, a receiver, an air reliever and a sealing seat. A drainage path is formed between a holding chamber and a drainage chamber which further comprises an inlet non-return valve disposed at a first mounting provision in the first housing and an outlet non-return valve disposed at a second mounting provision of the first housing.

The solenoid operated unit further comprises an electrical detection system, a mecha-electro-magnetic detection system, and a junction box interacting with an electronic control unit comprising a pulse width modulated (PWM) wave generator.

The first housing is disposed on the second housing on a mating surface of the second housing such that a first junction chamber of the first housing orients with a second junction chamber of the second housing and forms the junction box and a common axis of the first housing and the second housing becomes co-axial, consequently a first cylindrical chamber of the first housing and a second cylindrical chamber of the second housing forms the unified chamber.

The first housing corresponds to the sealing seat of undesired fluid, the electrical detection system, the mecha-electro-magnetic detection system. The second housing corresponding to the electromagnetic circuit. The pump-valve assembly is accommodated partially in the first housing and partially in the second housing. The solenoid operated unit is mounted at the bottom of a vessel.

The plunger moves from up to down, a sweeping volume with a cycle of a PWM electricity wave, while moving down the plunger creates a negative pressure in the sealing seat and while moving up a positive pressure gets created in the sealing seat and a negative pressure gets created at a rear end of the unified chamber and the plunger "sucks in" air from the air reliever.

The solenoid operated unit senses a real time position of a floating device, has a calibrated number of cycles N of the PWM electricity wave for a diagnostic metering. An error list decodes a variation of an actual number of cycles Na with reference to the calibrated number of cycles N of the PWM electricity wave.

DETAILED DESCRIPTION

The invention shall now be briefly described. The terms and illustration are merely for describing the invention and should not be construed to limit the invention. Properties of water are considered here to illustrate undesired fluid (6) while properties of diesel are considered to illustrate desirable fluid (5). However, the unit as per this invention is suitable for any two immiscible liquids of different specific gravity and electrical resistivity.

Figure 1:
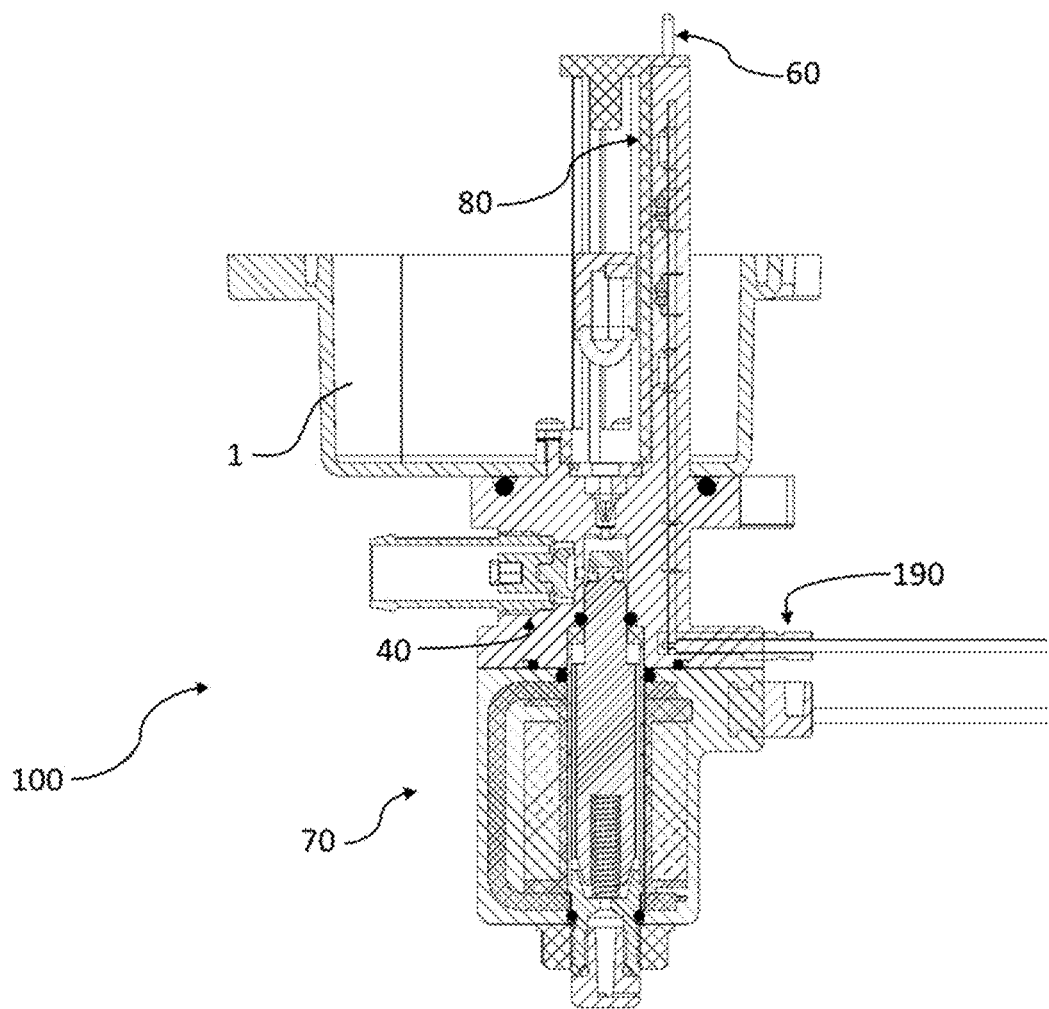
FIG. 1 is a sectional view of a solenoid operated unit as per present invention.

FIG. 1 the present invention is a solenoid operated unit (100) comprising:

A unified solenoid operated pump and valve unit (70),
A drainage path (40),
An electrical detection system (60),
A mecha-electro-magnetic detection system (80), and
A junction box (190) interacting with an Electronic Control Unit (ECU) comprising a PWM generator (not shown in this figure).

The solenoid operated unit (100) is mounted at the bottom of a vessel (1).

Figure 2:
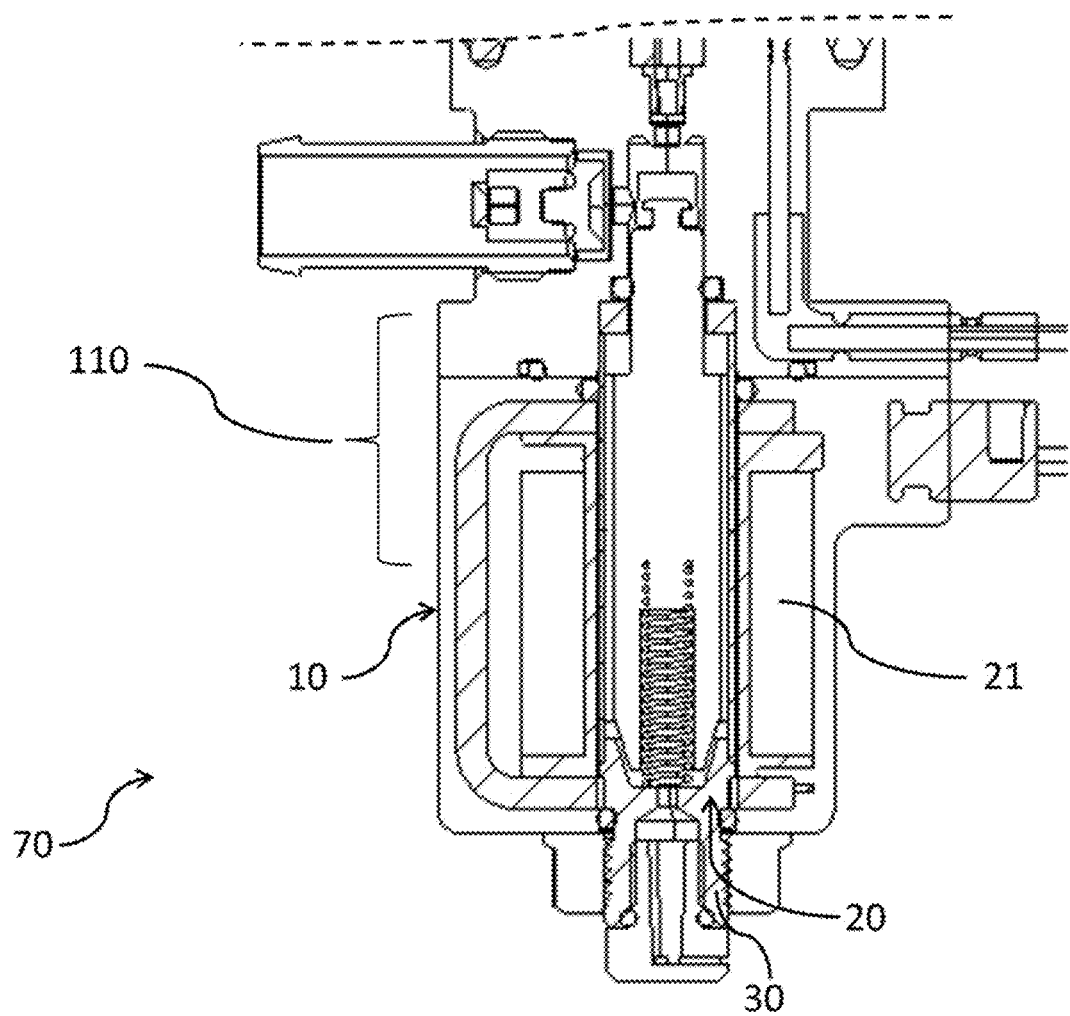
FIG. 2 is another sectional view of the solenoid operated unit.

FIG. 2, the unified solenoid operated pump and valve unit (70) comprises a combination housing (110), a solenoid coil circuit (10) and a pump-valve assembly (20).

Figure 3:
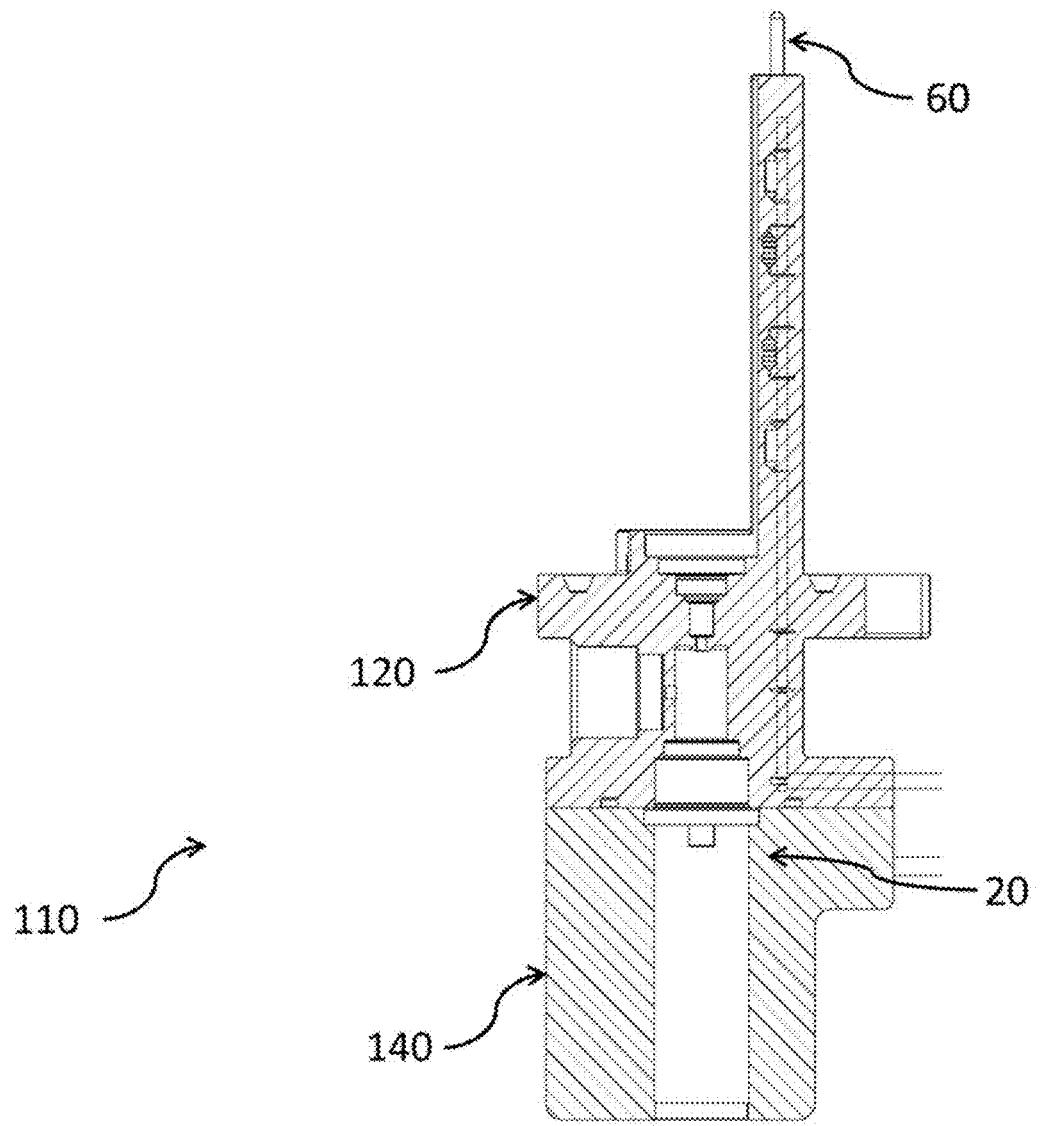
FIGS. 3 and 4 are partial sectional views of the solenoid operated unit.

FIG. 3, the combination housing (110) comprises a first housing (120) and a second housing (140). The first housing (120) primarily relates to the drainage path (40) of undesired fluid (6), the electrical detection system (60) and the mecha-electro-magnetic detection system (80) (not shown in this Figure) while the second housing (140) relates to the electromagnetic circuit. The pump-valve assembly (20) is accommodated partially in both—the first housing (120) and the second housing (140).

Figure 3A:
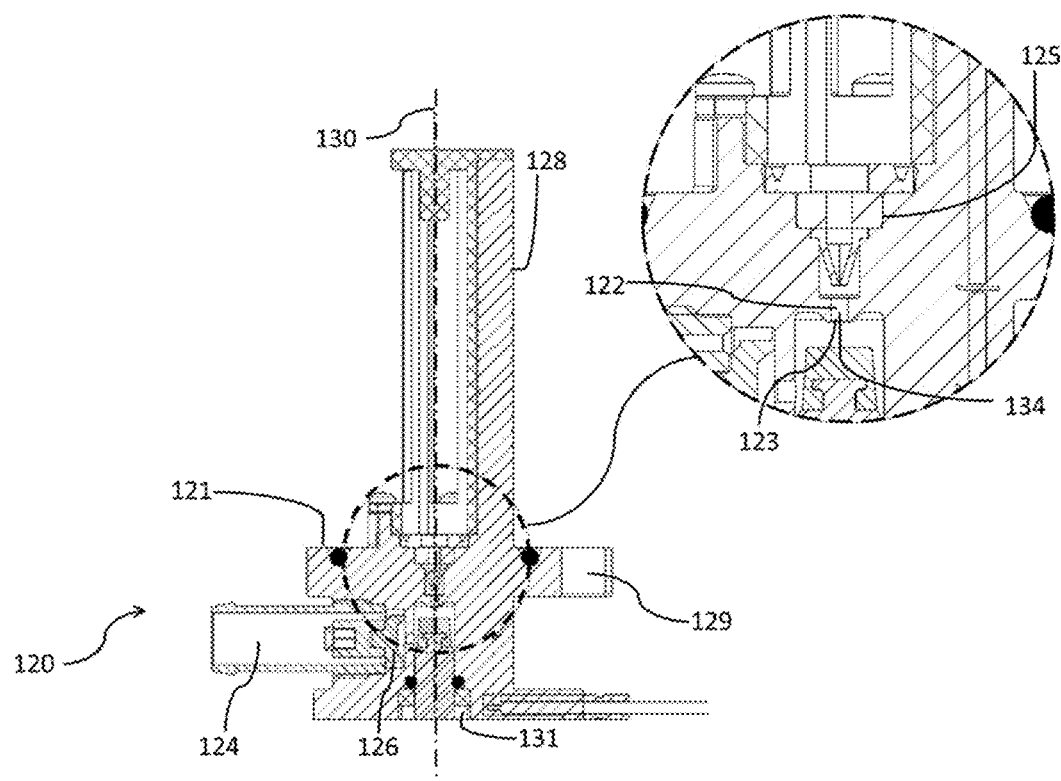
FIGS. 3A and 3B are sectional views of a first housing and a second housing of a combination housing of the solenoid operated unit respectively.

FIG. 3A, the first housing (120) comprises an interfacing surface (121), a holding chamber (122) having a bottom surface (123) and an orifice (134), a drainage chamber (124), a first mounting provision (125) and a second mounting provision (126). The first housing (120) further comprises an associated chamber (128), a first junction chamber (129), and a first cylindrical chamber (131). The first housing (120) further comprises a provision for mounting a modular float chamber (127), shown in FIG. 10, thereon.

Figure 3B:
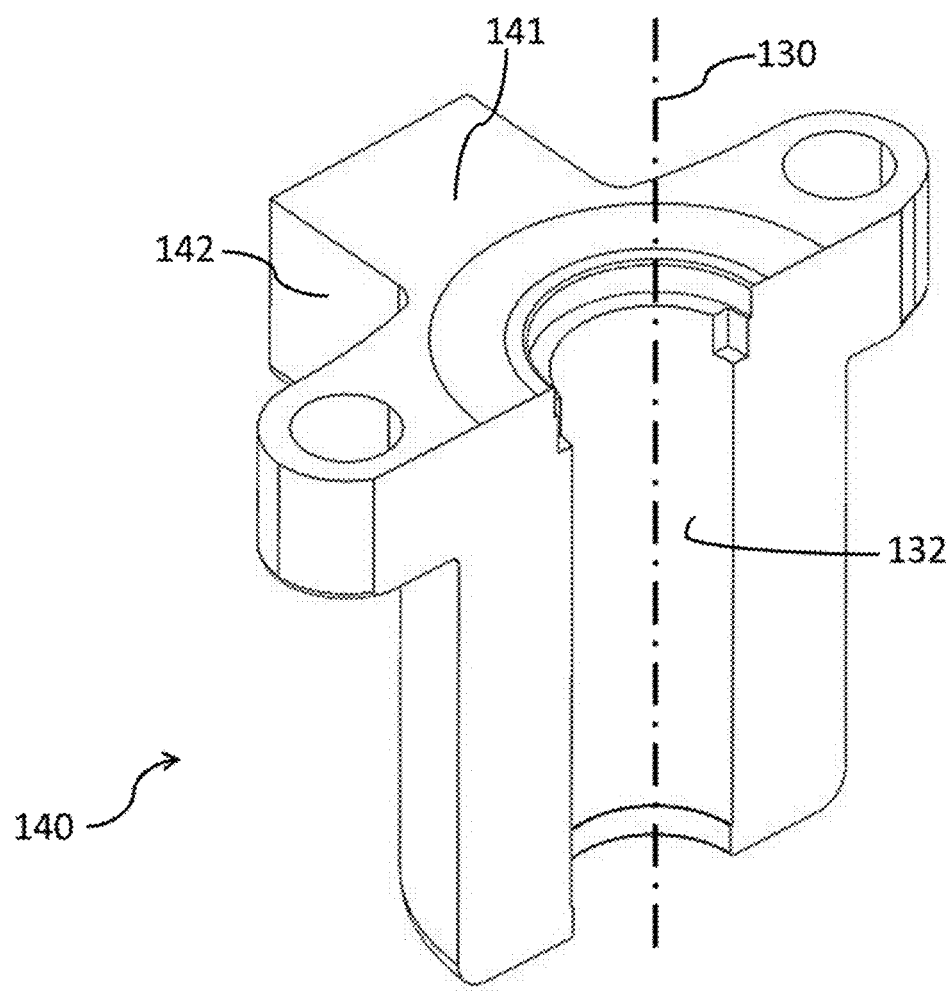

FIG. 3B, the second housing (140) comprises a mating surface (141), a second cylindrical chamber (132) and a second junction chamber (142).

Figure 4:
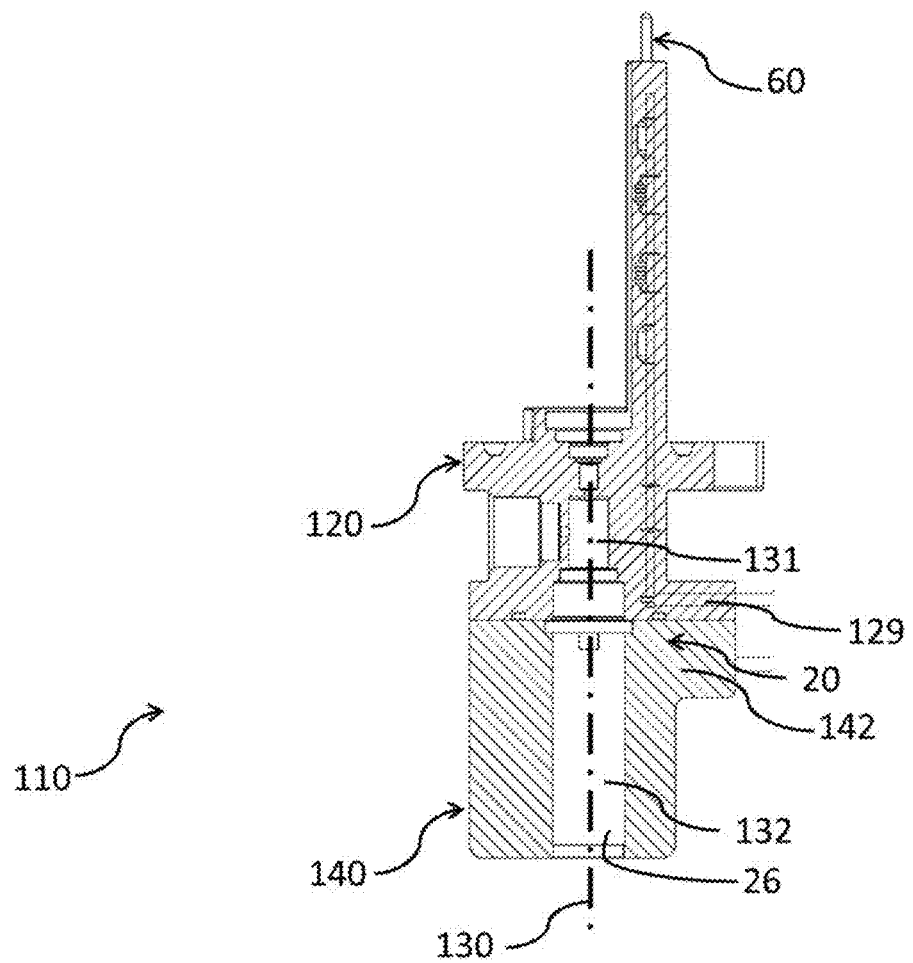

FIG. 4, the first housing (120) is disposed on the second housing (140) on the mating surface (141) such that the first junction chamber (129) orients with the second junction chamber (142) and forms the junction box (190), and a common axis (130) of each—the first housing (120) and the second housing (140) becomes co-axial, consequently the first cylindrical chamber (131) and the second cylindrical chamber (132) forms a unified chamber (26).

The solenoid coil circuit (10) is an electromagnetic circuit integrated with a fluid circuit.

Figure 4A:
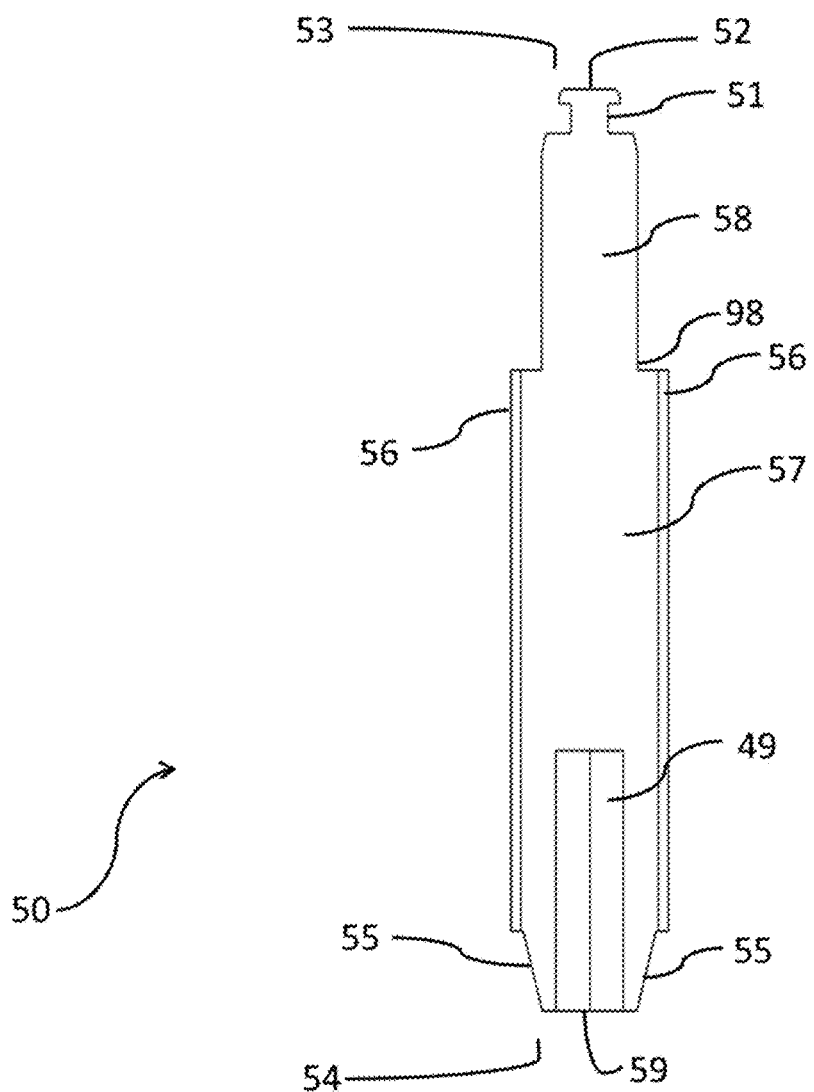
FIGS. 4A-4E show various parts of the solenoid operated unit.
Figure 4B:
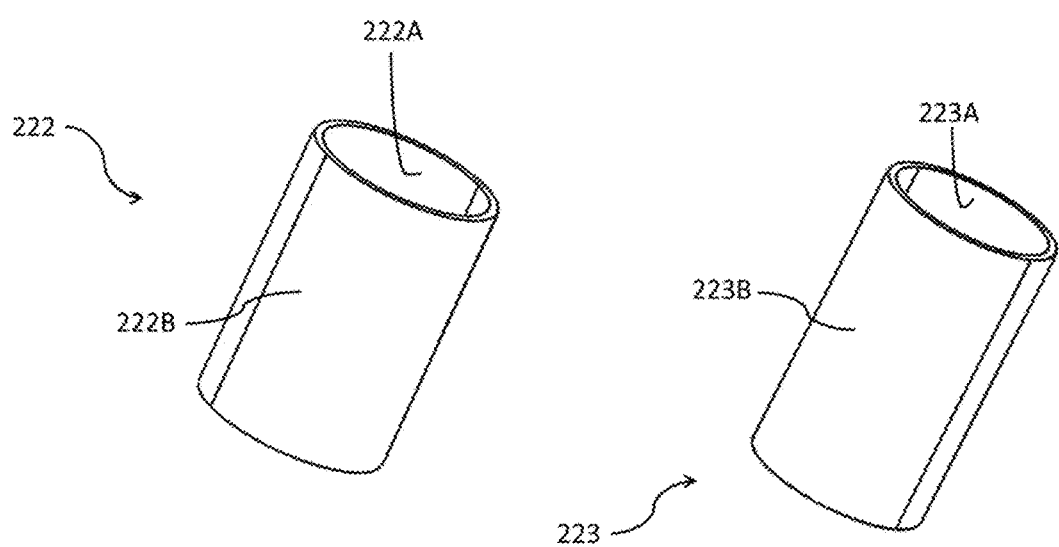
Figure 4C:
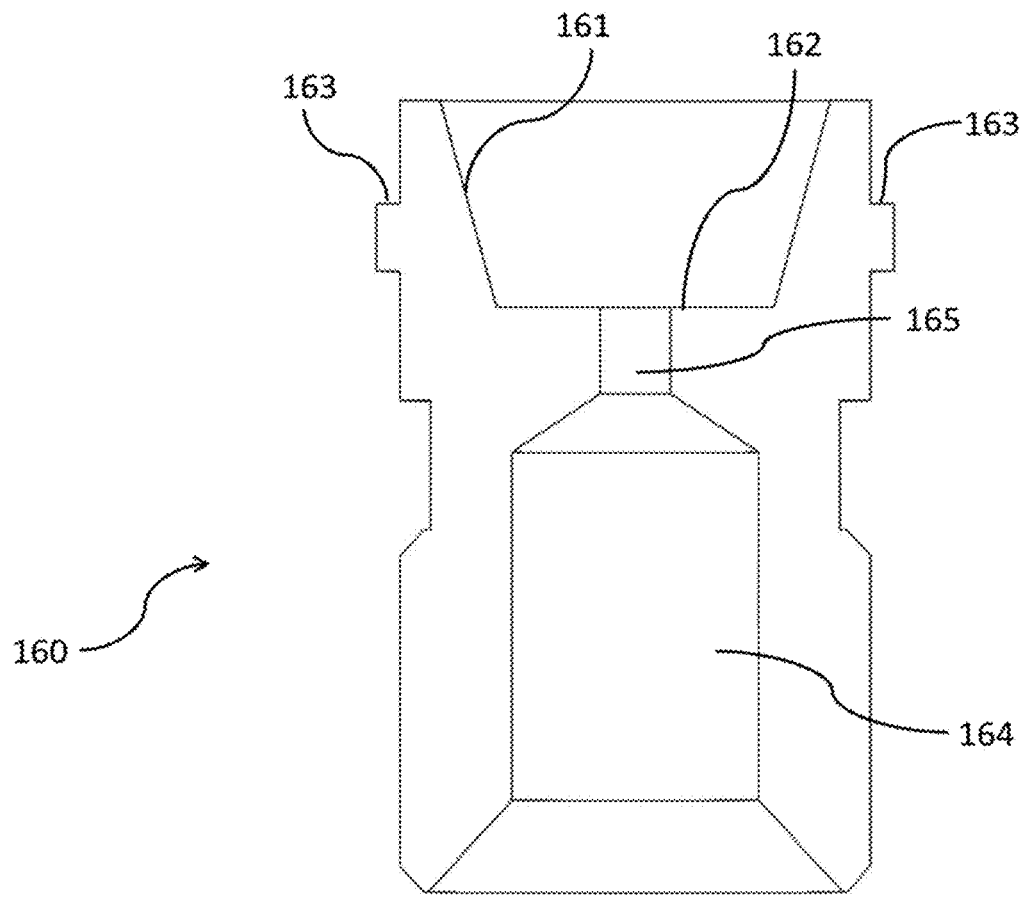

FIGS. 4A, 4B, 4C, the electromagnetic circuit involves a solenoid coil, a C-core, a plunger (50), a first liner (222) and a second liner (223) and a receiver (160) respectively.

Figure 5:
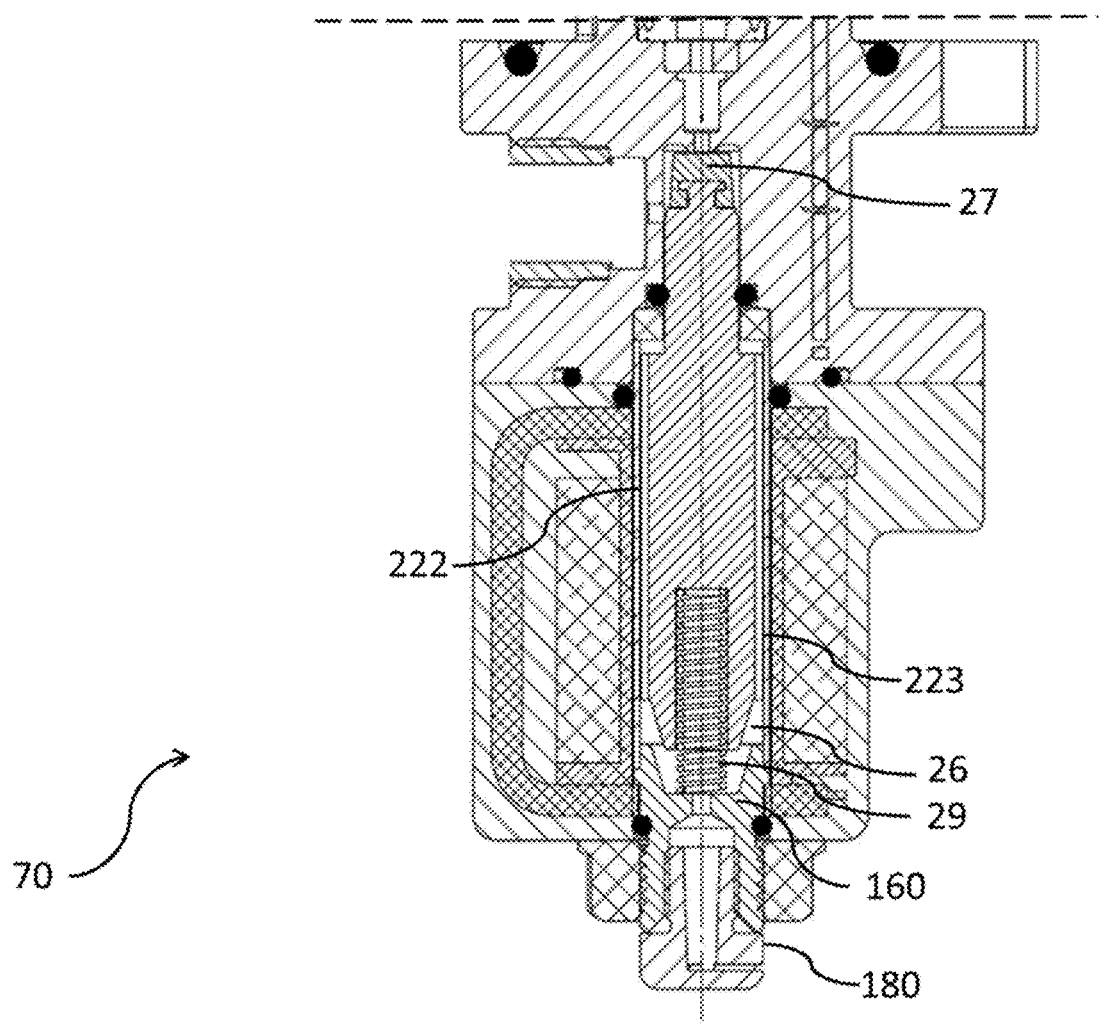
FIG. 5 is a sectional view of a pump-valve assembly.

FIG. 5, the pump-valve assembly (20) comprises the unified chamber (26) having the first liner (222) and the second liner (223), the plunger (50), the receiver (160) and an air reliever (180).

FIG. 4A, the plunger (50) is made of a ferromagnetic material with low residual magnetism retention, has a large cylindrical surface (57) and a small cylindrical surface (58), a head (52) with a neck (51) on the small cylindrical surface (58) towards a suction end (53), a first room (49) and an external frustum (55) towards a spring end (54). A plurality of longitudinal grooves (56) is provided on the large cylindrical surface (57).

FIG. 4B, the first liner (222) is a thin hollow cylinder made of a ferromagnetic, low frictional co-efficient metal or metal alloy, has a first liner inner surface (222A) and a first liner outer surface (222B). The second liner (223) is a thin hollow cylinder made of a non-magnetic, low frictional co-efficient metal or metal alloy, has a second liner inner surface (223A) and a second liner outer surface (223B).

FIG. 4C, the receiver (160) is made of a ferromagnetic material with low residual magnetism retention, has an internal frustum (161), a base (162), a peripheral seat (163) and a second room (164). There is provided an airway (165).

Figure 4D:
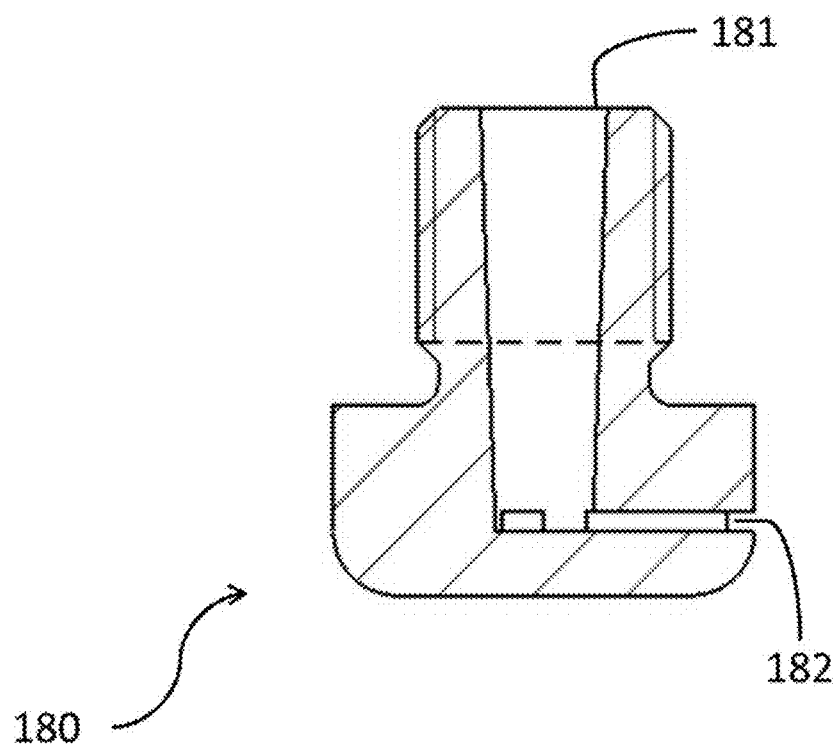

FIG. 4D, the air reliever (180) is essentially a bidirectional membrane that lets atmospheric air cross from an inside (181) to an outside (182) of the air reliever (180) depending on differential pressure on its two sides. This bidirectional membrane does not allow liquid and dust particles to cross from the outside (182) to inside (181) of the air reliever (180).

Figure 4E:
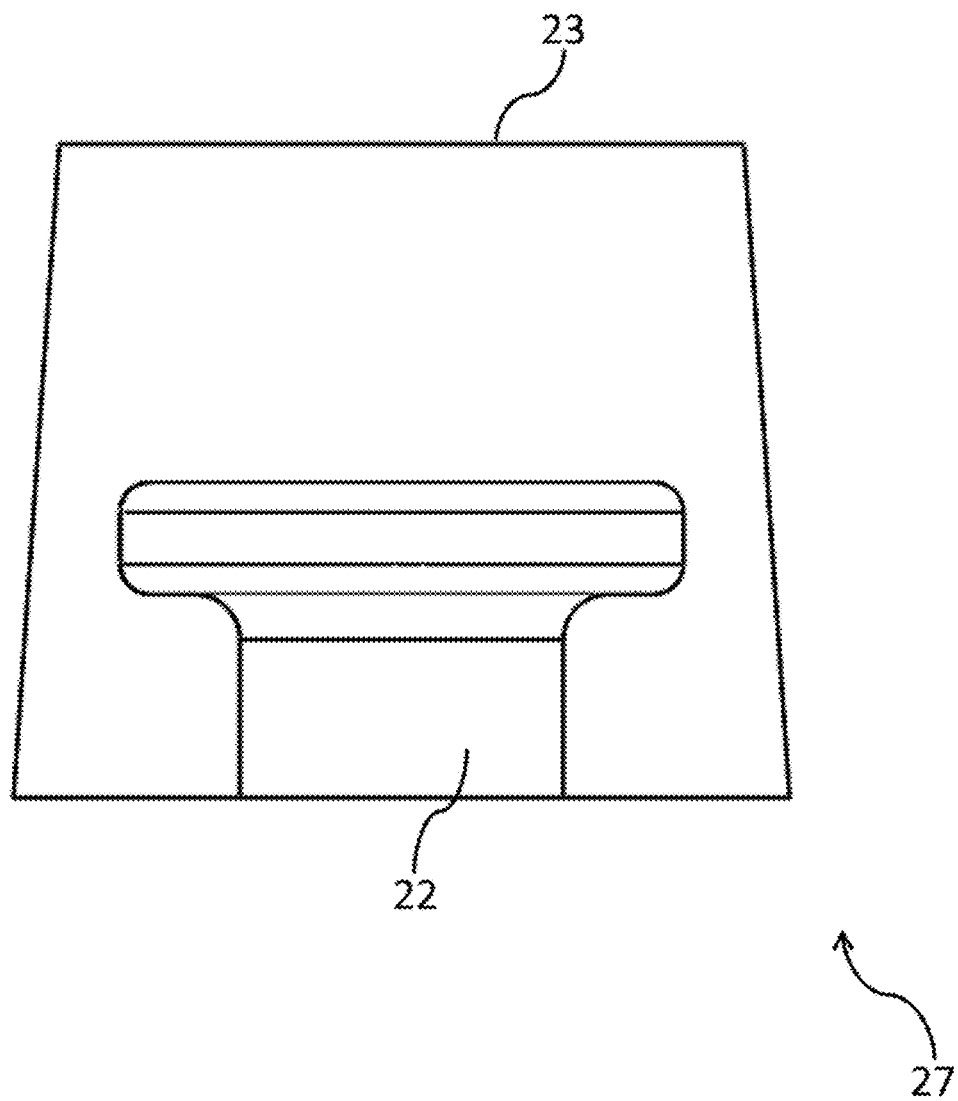

FIG. 4E, a sealing seat (27) made of rubber, whether natural or synthetic, of durometer hardness more than 40, having a sealing surface (23) and a cavity (22) complementary in profile to the head (52) and the neck (51) of the plunger (50), is mounted on the plunger (50) by elastic deformation.

The receiver (160) is rigidly disposed at a lower end of the second housing (140). The air reliever (180) is disposed in the second room (164) of the receiver (160). The second liner (223) sits on the peripheral seat (163) of the receiver (160) such that the second liner outer surface (223B) of the second liner (223) sits against a wall of the unified chamber (26). The first liner (222) sits adjacent to the second liner (223) such that the first liner outer surface (222B) of the first liner (222) sits against the wall of the unified chamber (26).

Figure 6:
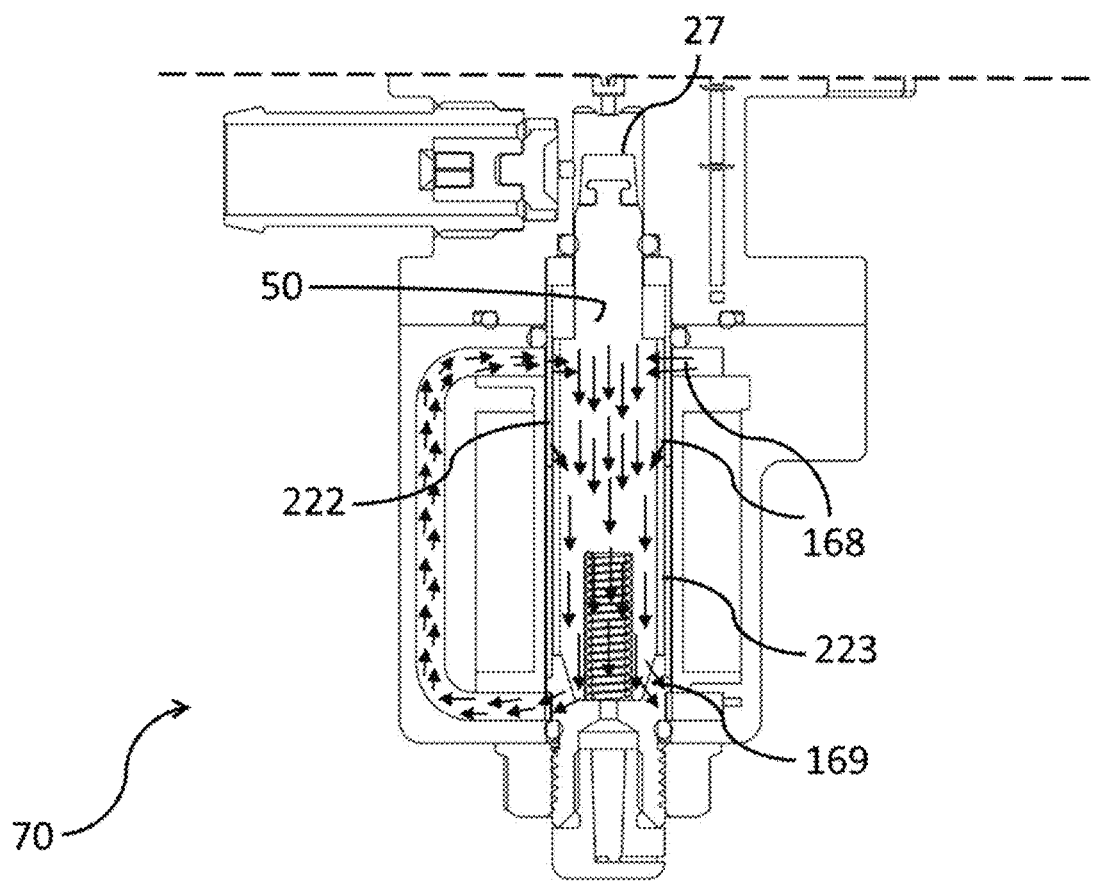
FIG. 6 shows magnetic lines of forces acting in the solenoid operated unit.

The plunger (50) with the sealing seat (27) linearly moves glidingly on the first liner inner surface (222A) of the first liner (222) and the second liner inner surface (223A) of the second liner (223) under an influence of the magnetism and a compression spring (29). The first liner (222) being made of the ferromagnetic material pulls in stray magnetic lines of forces (168) so that there is maximum transaction of magnetic lines of forces (169) between the external frustum (55) of the plunger (50) and the internal frustum (161) of the receiver (160). FIG. 6.

Figure 7:
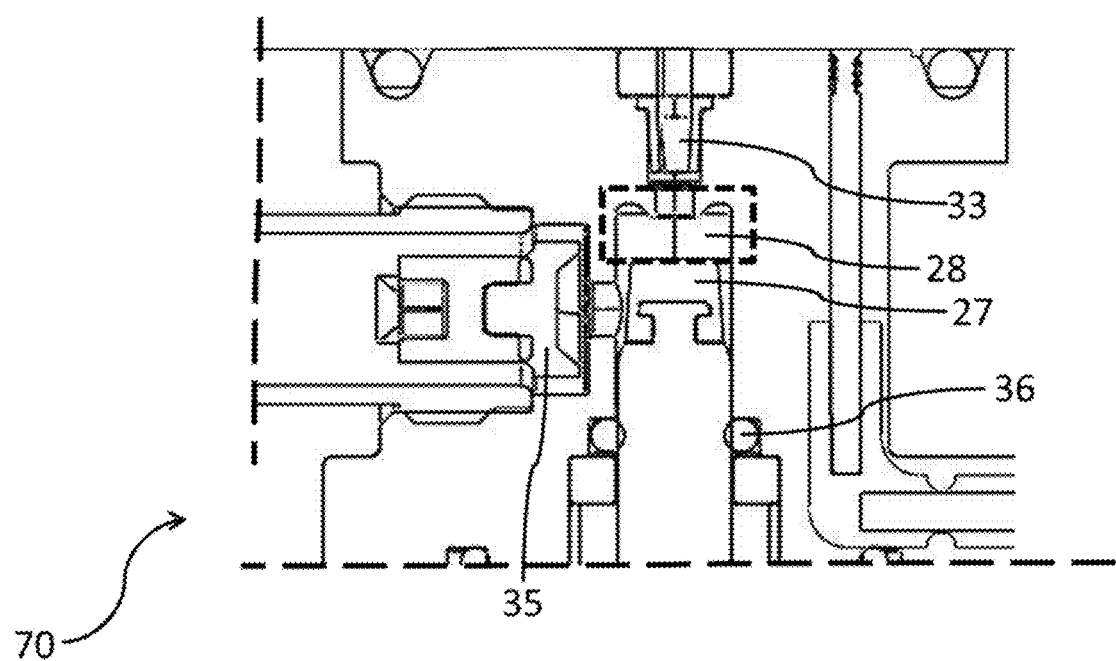
FIG. 7 shows a sweeping volume.

The plunger (50) can move up till the sealing surface (23) of the sealing seat (27) seals the orifice (134) at the bottom surface (123) of the holding chamber (122), and can move down till a frustum base (59) of the plunger (50) hits the base (162) of the receiver (160). FIG. 7, a volume above the sealing surface (23) of the sealing seat (27) up to the bottom surface (123) of the holding chamber (122), when the plunger (50) has moved down, shown in dotted box, is termed as a sweeping volume (28). The sweeping volume (28) is fluidically insulated from the remaining close channel by a seal (36).

When a solenoid coil (21) is de-energized, the compression spring (29) keeps the frustum base (59) of the plunger (50) pushed away and up and consequently the suction end (53) of the plunger (50) occupies the sweeping volume (28), while the sealing surface (23) of the sealing seat (27) seals, that is, fluidically blocks the orifice (134).

When the solenoid coil (21) is energized, the electromagnetic forces overcome the force of the compression spring (29) and the plunger (50) travel towards a rear end (30) of the unified chamber (26).

Figure 8:
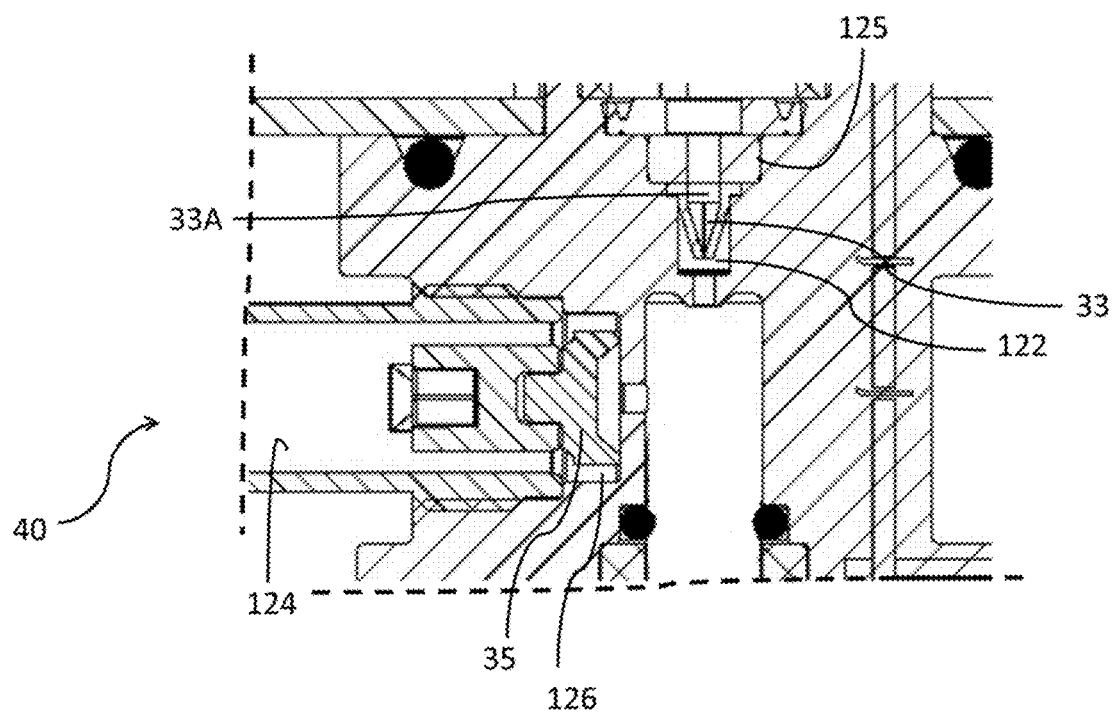
FIG. 8 shows a drainage path between a holding chamber and a drainage chamber.

FIG. 8, the drainage path (40) comprises:
an inlet non-return valve (33) disposed at the first mounting provision (125) in the first housing (120),
the holding chamber (122),
an outlet non-return valve (35) disposed at the second mounting provision (126) of the first housing (120), and
the drainage chamber (124).

When the solenoid coil (21) is energized with an alternating current electricity of square wave of magnitude alternating between ZERO Volts and a finite value, say 24 Volts, hereinafter termed as HIGH Volts, then the solenoid coil (21) behaves as energized when the voltage wave is HIGH, and behaves as un-energized when the voltage wave is ZERO. Consequently, the plunger (50) travels to and fro in the unified chamber (26). While moving down, the plunger (50) creates a negative pressure in the unified chamber (26) and can "suck" a fluid from the inlet non-return valve (33). While moving up, a positive pressure gets created in the unified chamber (26) while at the rear end (30), the air inside the second cylindrical chamber (132) moves around the plunger (50) i.e. during downward movement of the plunger (50), the air from the unified chamber (26) moves towards the rear end (30) and vice versa. The reliever (180) either drains or sucks air in case of thermal expansion or contraction of the air inside the unified chamber (26), and providing need of breathing to that area.

The inlet non-return valve (33) of the drainage path (40) opens when there is the negative pressure in the unified chamber (26) while the outlet non-return valve (35) opens when there is the positive pressure in the unified chamber (26).

Figure 9:
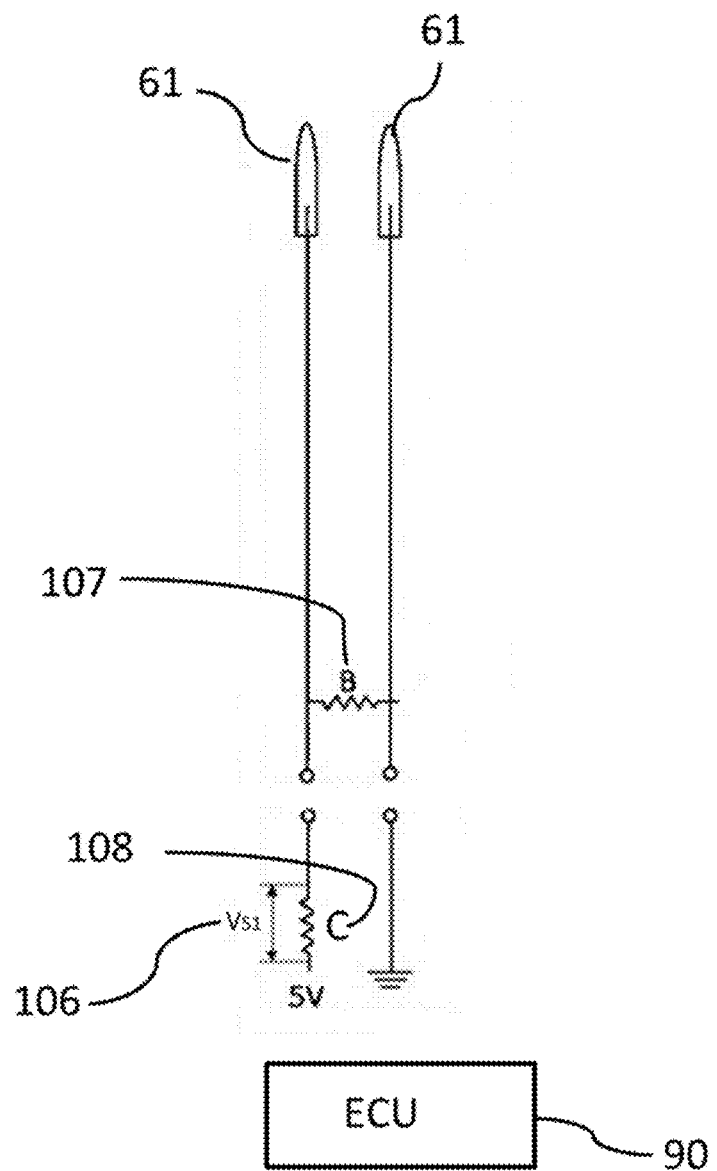
FIG. 9 shows an electrical schematic of an electrical detection system unit.

FIG. 9, the electrical detection system (60), housed in the associated chamber (128) of the first housing (120) comprises a electrical circuitry assembly having a plurality of bare probes (61) placed at a calculated distance between each other, which are connected to an electrical circuitry as shown in FIG. 9. FIG. 14B shows a corresponding electrical circuit assembly (74). When the plurality of bare probes (61) has the desired liquid (5) around them, the output voltage is nearly equal to a source voltage Vs1 (106); which drops to about 50% value when the plurality of bare probes (61) have the undesired fluid (6) around them.

Figure 9A:
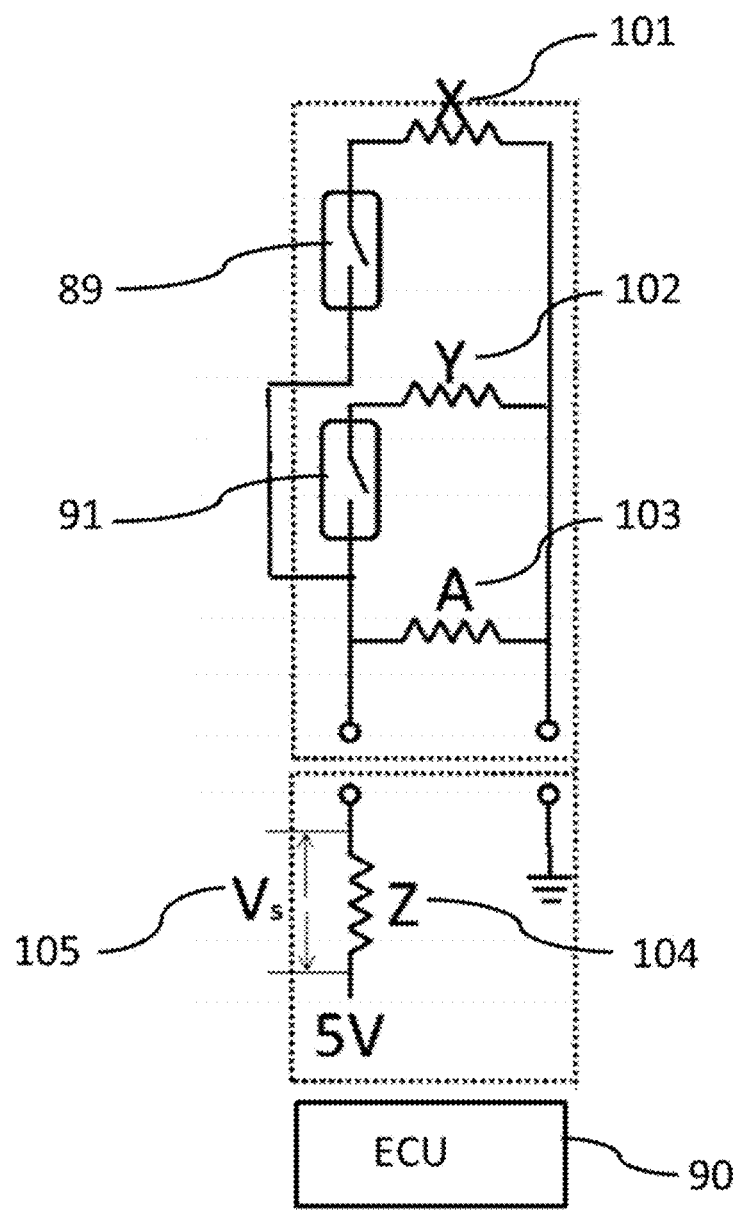
FIG. 9A is an electrical schematic of the electromagnetic detection system unit.
Figure 10:
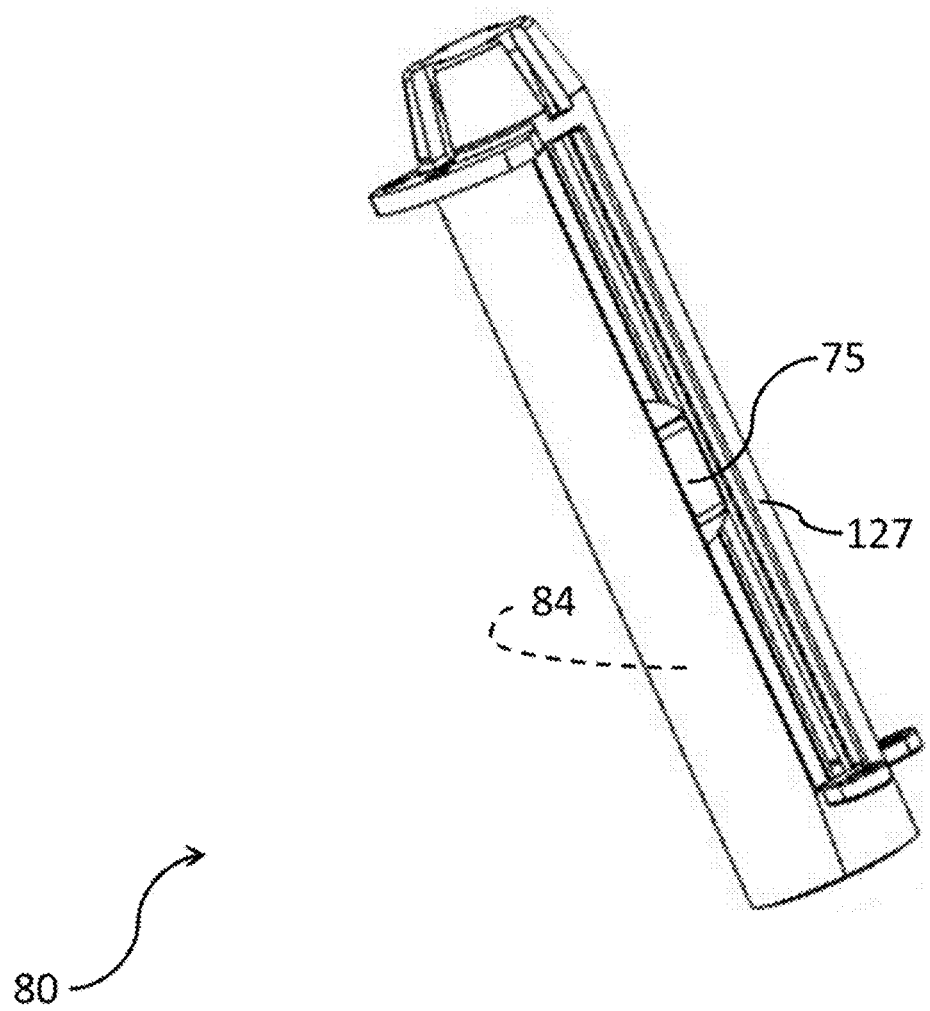
FIG. 10 shows a mecha-electro-magnetic detection system.
Figure 14:
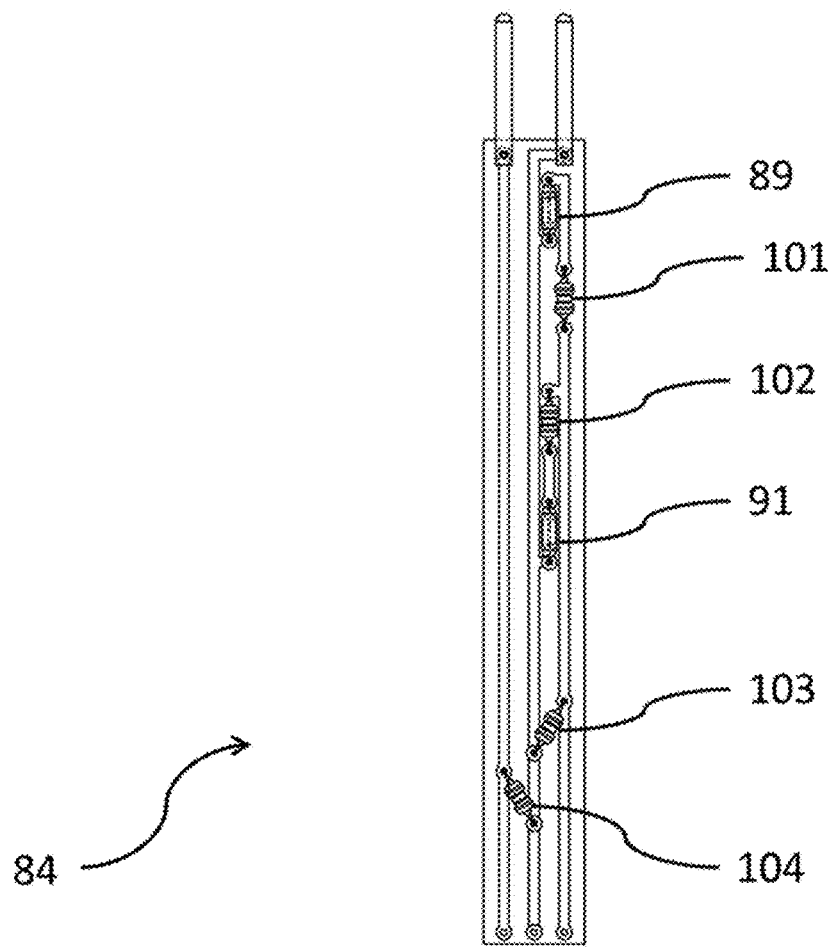
FIG. 14 shows an electro-magnetic circuitry assembly.

FIGS. 10 and 14, the mecha-electro-magnetic detection system (80) comprises:
the modular float chamber (127),
a floating device (75), and
an electro-magnetic circuitry assembly (84) comprising an upper magnetic switch (89), a lower magnetic switch (91), a first resistance X (101), a second resistance Y (102), a third resistance A (103) and a fourth resistance Z (104), electrically connected as shown in FIG. 9A. Vs (105) is a sensing voltage which is sensed across the fourth resistance Z (104) at the sensing circuit. The fourth resistance Z (104) is a part of the mecha-electro-magnetic detection system (80), though may or may not be a part of solenoid operated unit (100).

When both of the upper magnetic switch (89) as well as the lower magnetic switch (91) are open, it implies that the floating device (75) is in between the upper magnetic switch (89) and the lower magnetic switch (91) and the voltage Vs (105) shall be consequent to a current be passing from the third resistance A (103) and the fourth resistance Z (104). When the upper magnetic switch (89) is close due to the floating device (75) reaching its vicinity, then the voltage Vs (105) shall be consequent to a current passing from the first resistance X (101) also which is in parallel to the third resistance A (103), and the fourth resistance Z (104).

When the lower magnetic switch (91) is close due to the floating device (75) reaching its vicinity then the voltage Vs (105) shall be consequent to a current passing from the second resistance Y (102) which is in parallel to the third resistance A (103), and the fourth resistance Z (104). Thus the present invention senses a real-time position of the floating device (75) with a two wire system. In the event there is an electrical disconnection, then the voltage Vs (105) will be nearly Zero Volts, indicating a breakage of the electrical system. A magnitude of the voltage Vs (105) can be used to interpret any of the resistances getting open circuited or short circuited, or any anomaly in the electromagnetic circuitry assembly (84).

Figure 9B:
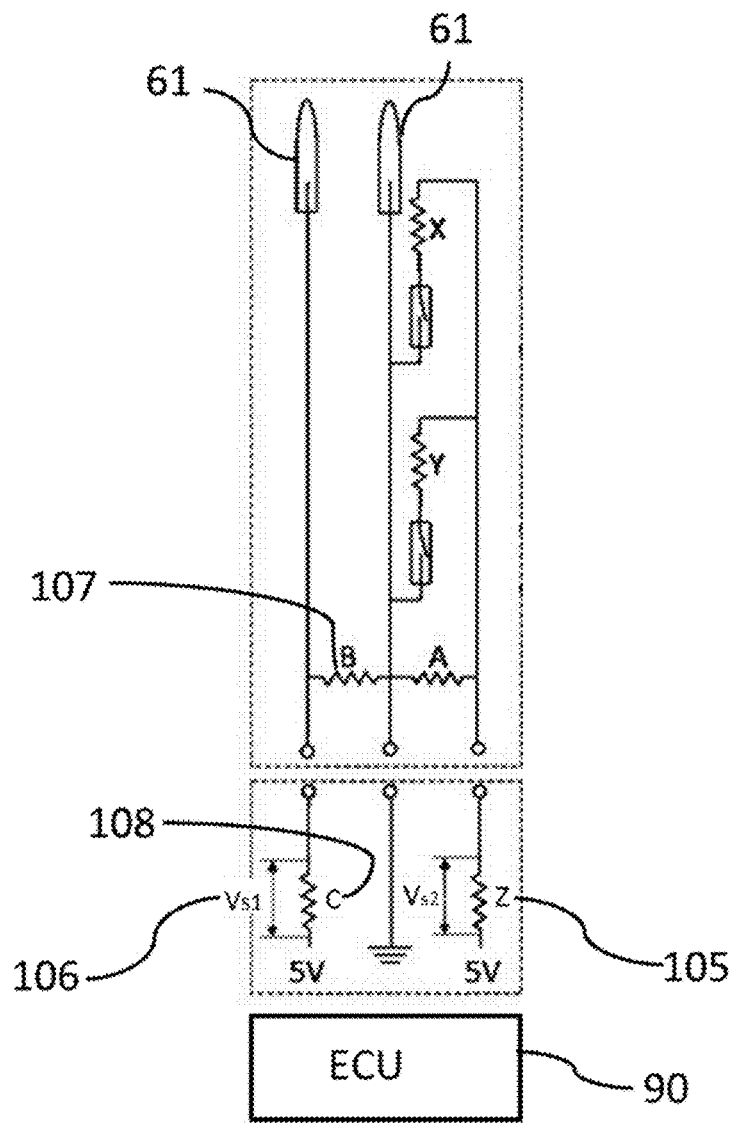
FIG. 9B shows an electrical schematic of a unit circuitry assembly.
Figure 14A:
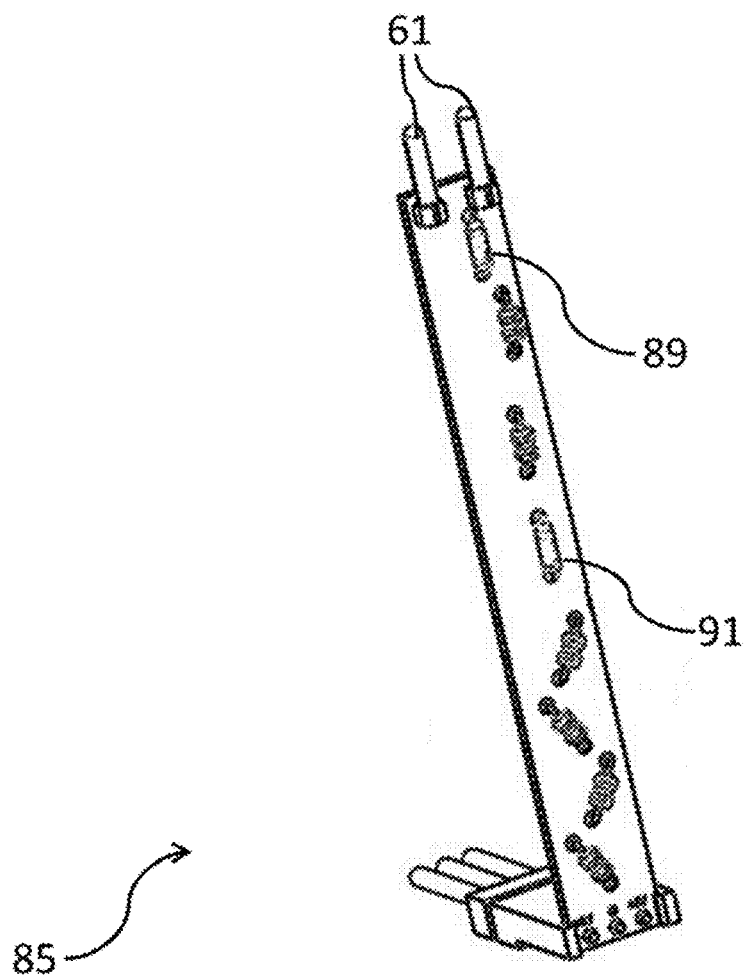
FIG. 14A shows a unit circuitry assembly with an integrated electrical circuitry assembly and the electro-magnetic circuitry assembly.
Figure 14B:
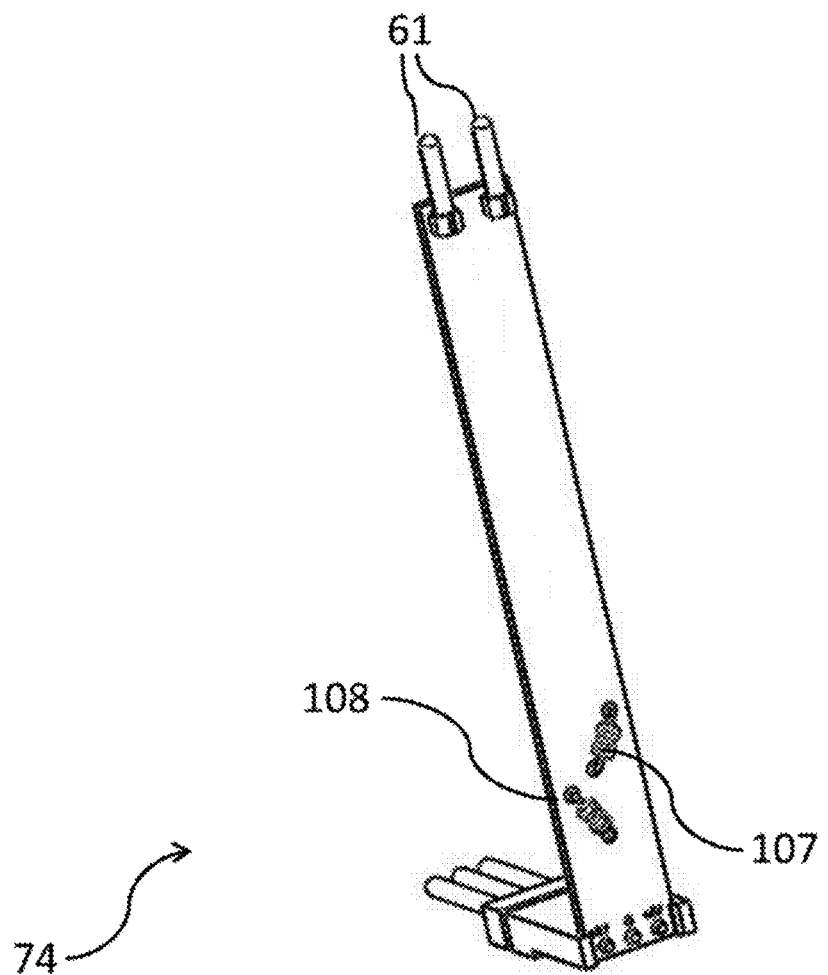
FIG. 14B shows an electrical circuit assembly.

The electrical circuitry assembly (74), FIG. 14B, and the electro-magnetic circuitry assembly (84), FIG. 14, are integrated to a unit circuitry assembly (85), FIG. 14A, as per schematic diagram shown in FIG. 9B; and is encapsulatedly housed in the associated chamber (128) of the first housing (120).

Figure 10A:
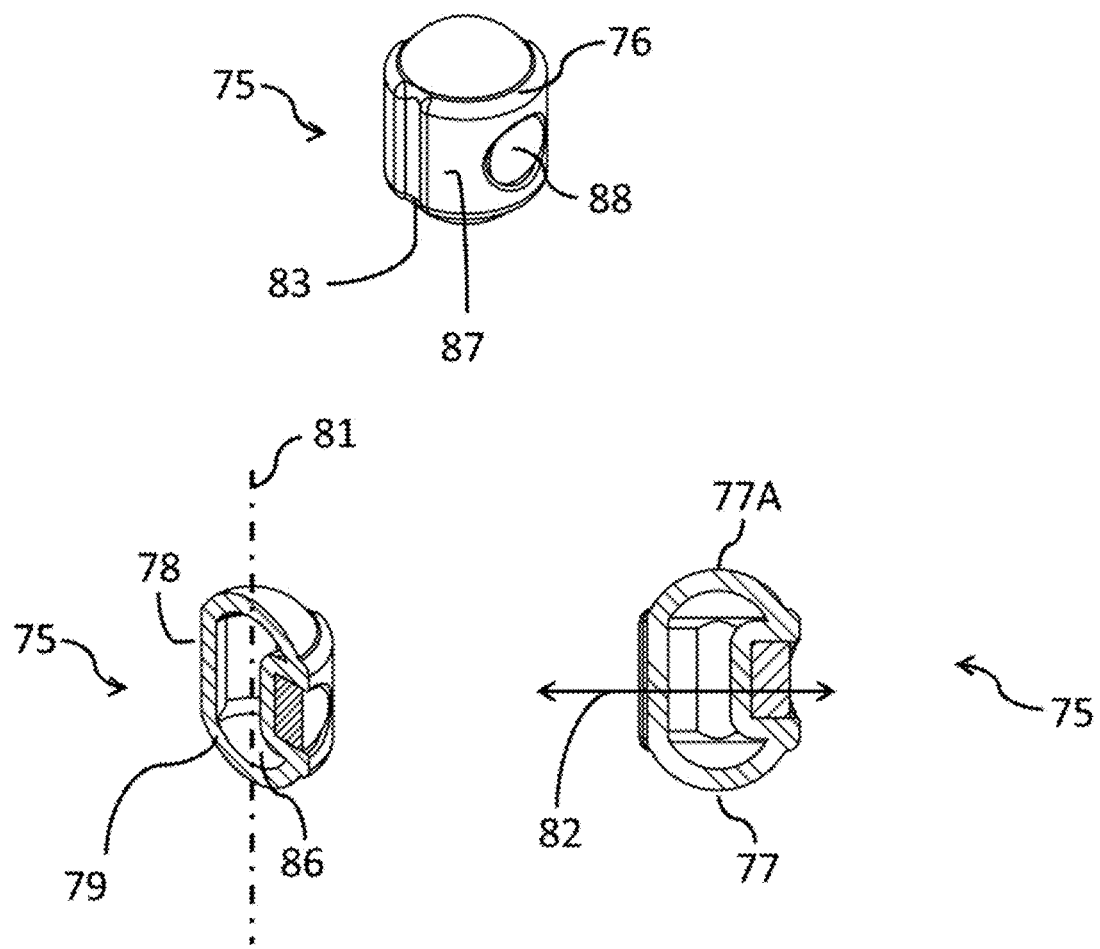
FIG. 10A shows one embodiment of a floating device.
Figure 10B:
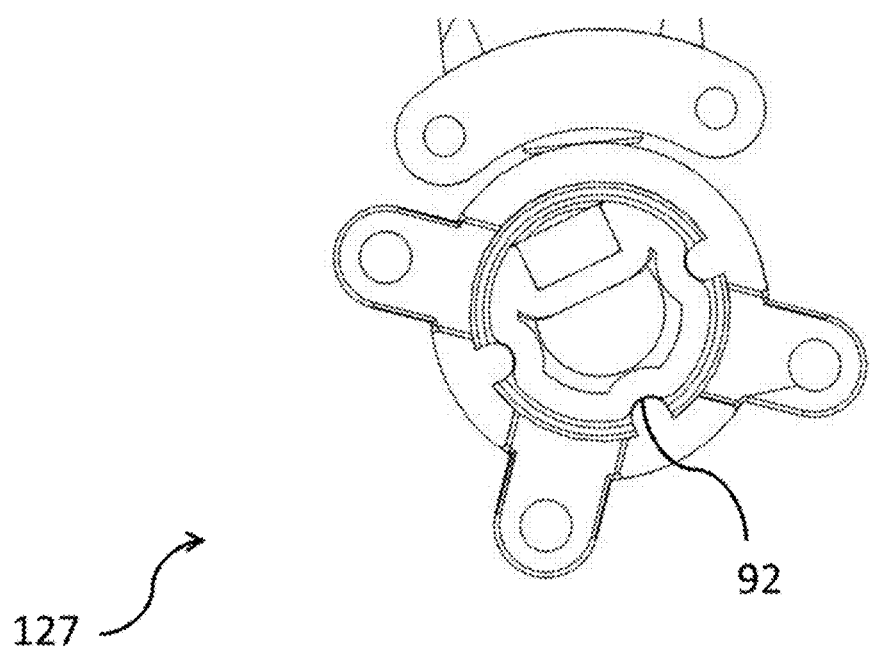
FIG. 10B shows a modular float chamber.

FIGS. 10A, 10B, the floating device (75) comprises a floater (76) and a permanent magnet (88). The mass and volume of the floating device (75) is such that the floating device (75) floats in the undesirable liquid (6) up to a calculated height as shown in FIG. 8, and sinks in the desirable liquid (5). The floating device (75) has spherical end (77) at least at one end and has a cylindrical part (78). The floater (76) is symmetrical in shape about a longitudinal plane (79), shown hatched in FIG. 10A and containing a longitudinal axis (81) of the cylindrical part (78). Also shown a radial plane (82), denoted by a line, which is passing through a middle of the cylindrical part (78) of the floater (76). The cylindrical part (78) has a plurality of longitudinal recess (83). The permanent magnet (88) is disposed on a surface (87) of the cylindrical part (78) symmetrically about the longitudinal plane (79) but asymmetrically about the radial plane (82) and oriented such a way that magnet inside is in front of magnet switch.

The modular float chamber (127) comprises a compatible provision for getting mounted on the first housing (120). The modular float chamber (127) further comprises a plurality of longitudinal projections (92) complementary to the plurality of longitudinal recess (83) on the floater (76) constraining any random movement of the floater (76) except along the longitudinal axis (81).

There is entrapped a prescribed volume of an atmospheric air (86) in the floater (76) and it then becomes possible to use a wide variety of engineering plastics or other materials to arrive at the required mass and volume of the floating device (75) commensurate with use for petrol or diesel and fuels of different specific gravities, lower than water.

In an embodiment, the mass and volume of the floating device (75) corresponds to the desired fluid (5) being diesel.

In another embodiment, the mass and volume of the floating device (75) corresponds to the desired fluid (5) being petrol.

In another embodiment, the floating device (75) is asymmetrical about the radial plane (82) such that a "First Fluid" spherical end (77) faces the drainage path (40) when used for a desirable first fluid; while a "Second Fluid" spherical end (77A) faces the drainage path (40) when used for desirable second fluid.

Figure 10C:
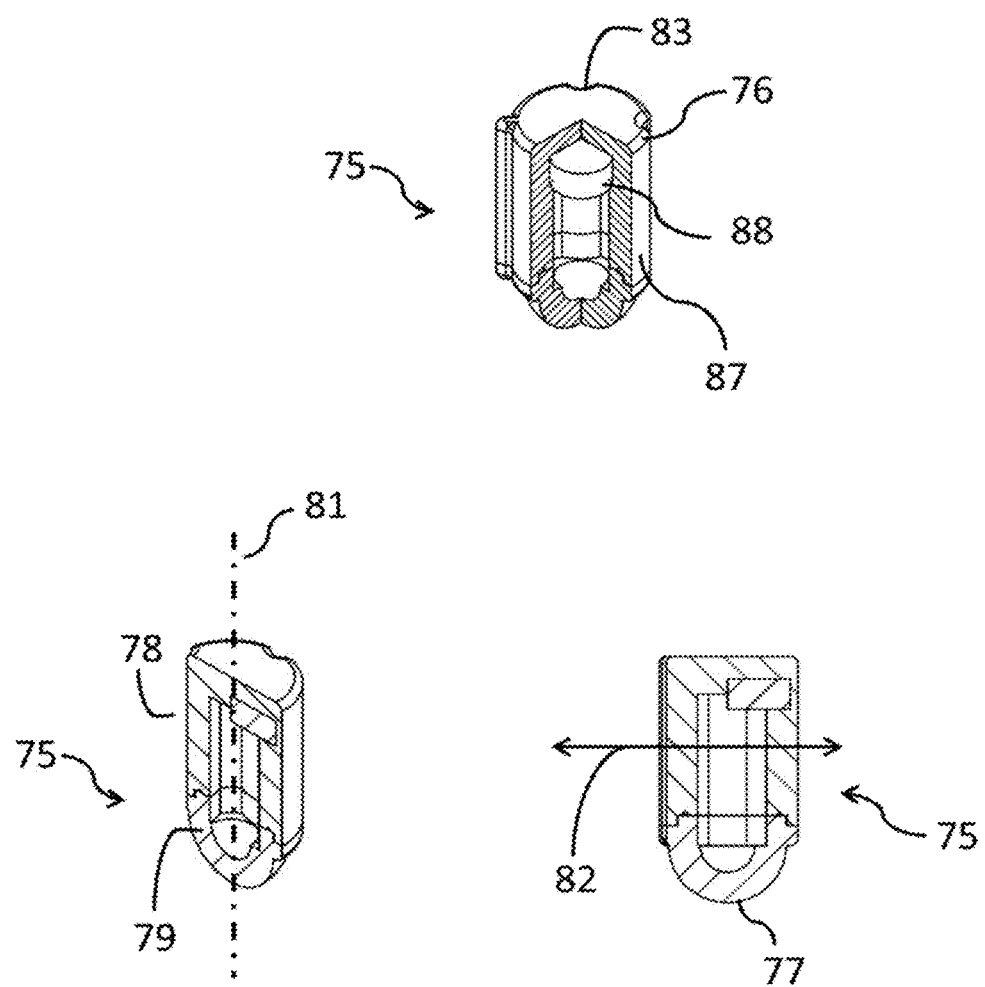
FIG. 10C shows another embodiment of the floating device.

FIG. 10C, in another embodiment, the floating device (75) is disposed slidably in the modular float chamber (127) only in one direction, or unidirectionally.

FIGS. 9, 9A and 9B, the output of the mecha-electro-magnetic detection system (80) and the electrical detection system (60) is fed to an electronic control unit (90) which energizes and de-energizes the solenoid coil (21) when the detection systems (60 and 80) sense the undesired fluid (6).

Figure 11:
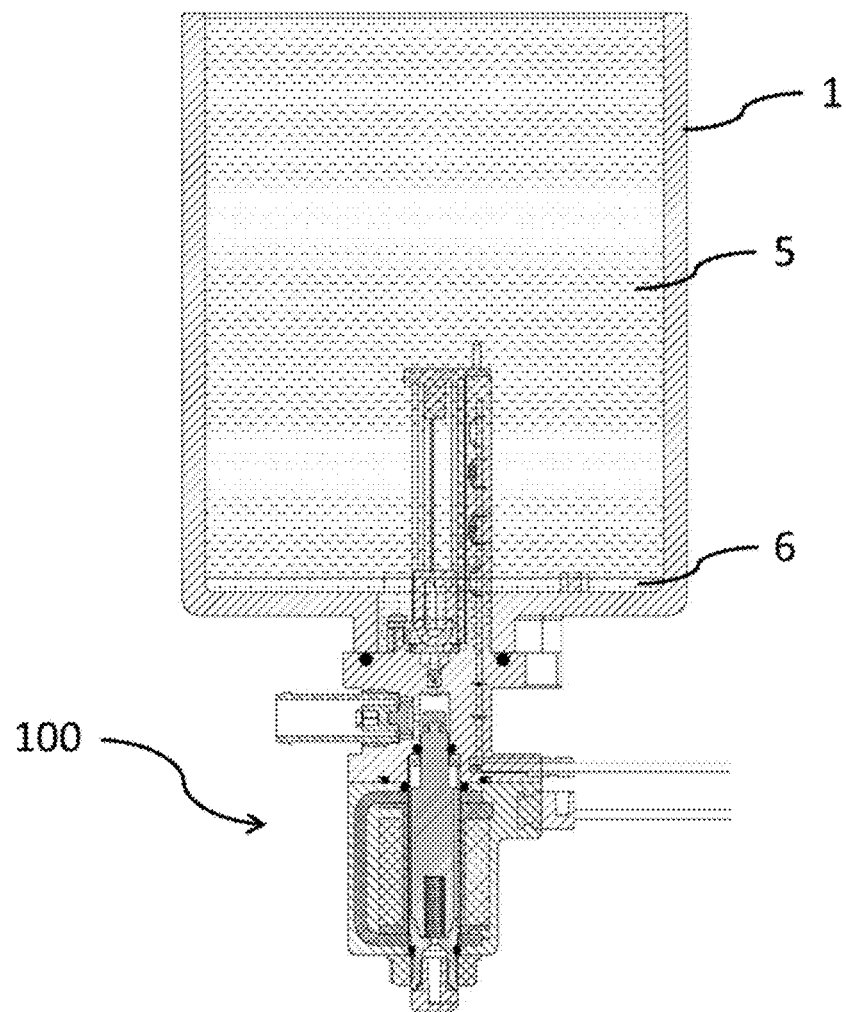
FIGS. 11 and 12 are sectional views of the solenoid operated unit mounted below a vessel illustrating a movement of floating device in a desirable and an undesirable fluid.
Figure 12:
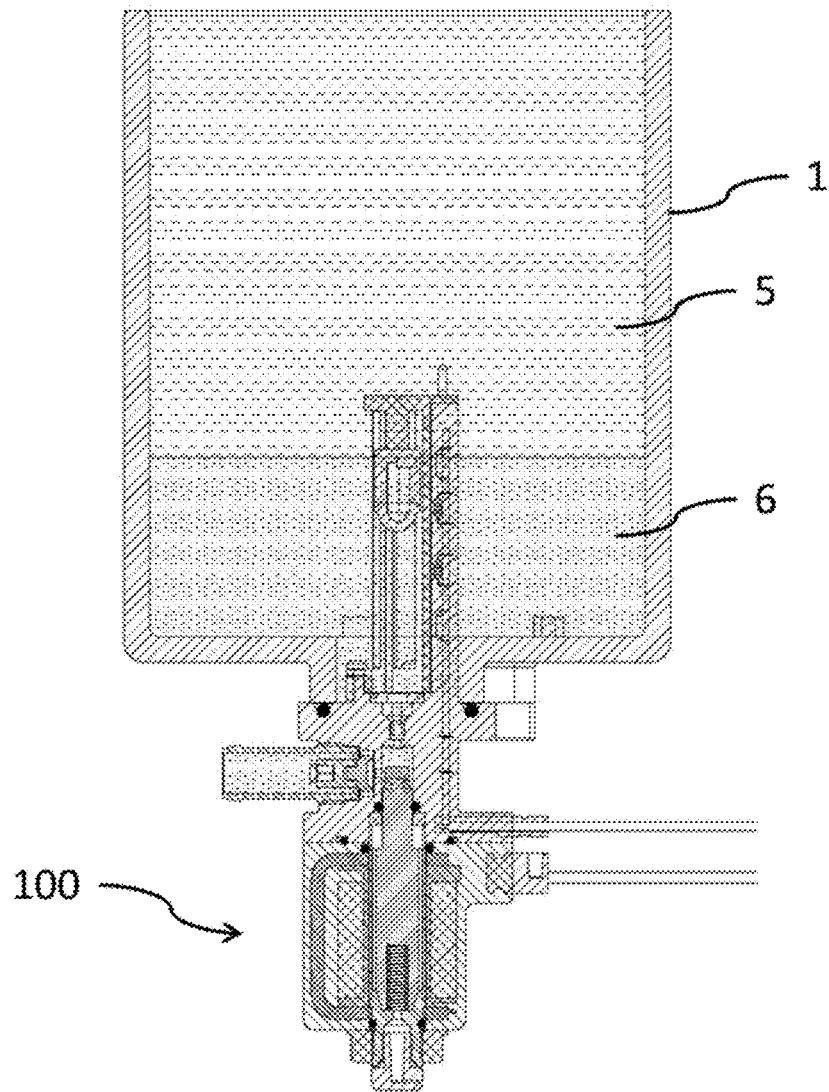

FIGS. 1, 11 and 12, when the solenoid operated unit (100) as per present invention is mounted at the bottom of the vessel (1) through the interfacing surface (121) of the first housing (120), with the fluid (5,6) in the vessel (1), the plurality of bare probes (61) of the electrical detection system (60) and the floating device (75) of the mecha-electro-magnetic detection system (80) projects up and are surrounded by the fluid (5,6). Constructional dimensions of the electrical detection system (60) and the mecha-electro-magnetic detection system (80) are such coordinated that when the plurality of bare probes (61) are surrounded by the desired fluid (5), the spherical end (77) of the floating device (75) sits and seals an inlet opening (33A) shown in FIG. 8, of the inlet non-return valve (33) and the permanent magnet (88) of the floating device (75) is considerably below and therefore away from the upper magnetic switch (89), which is commonly a reed switch or hall switch and in front of lower magnetic switch (91).

When the undesired fluid (6) starts accumulating more than a permissible limit, the floating device (75) lifts up, however the pressure of the fluid column may or may not be sufficient to push the undesired fluid (6) out of the outlet non-return valve (35). When the undesired fluid (6) is adequate to surround the plurality of bare probes (61) and/or lift up the floating device (75) so that the permanent magnet

(88) is in front of upper magnetic switch (89), then the solenoid coil (21) is energized and the plunger (50) starts moving to and fro creating negative pressure and positive pressure alternately as described above. When negative pressure is created, the undesired fluid (6) of a volume equal to that of the sweeping volume (28) is drawn into the drainage path (40). When positive pressure is created, the undesired fluid (6) pushes open the outlet non-return valve (35) and exits the drainage path (40). Hence the solenoid operated unit (100) as per present invention does not depend on a fluid column pressure for bleeding the undesired fluid (6).

Figure 13:
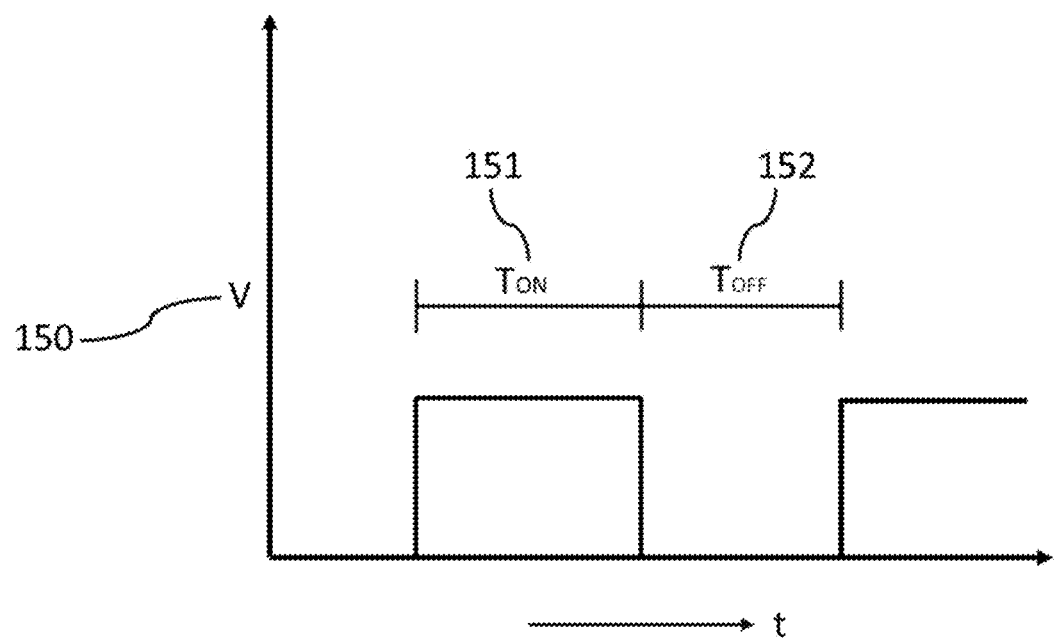
FIG. 13 shows a Pulse Width Modulated (PWM) wave.

Due to the plunger (50) moving up and down in consonance with an alternating square wave with pre-calibrated time $T_{on}$ (151) and $T_{off}$ (152) (as seen from FIG. 13) of each electrical pulse, known as a pulse width modulated (PWM) wave, a number of a pair of down and up movements is precisely known and is equal to a number of PWM waves, called a number of cycles N, seen by the solenoid coil (21). The solenoid operated unit (100) as per present invention thus meters the undesired fluid (6) drained out.

The solenoid operated unit (100) as per present invention provides diagnostic metering as follows: For a given design of the vessel (1) in which the solenoid operated unit (100) as per present invention is mounted for the first time (during validation or design stage) the number of cycles N required are determinable to drain the certain volume of water from the vessel (1). Thus N cycles corresponds to the floating device (75) travelling from a top to a bottom position. In the event significantly more than N cycles are required to drain, it indicates an efficiency of the solenoid operated unit (100) has reduced and it may soon stop working unless examined and serviced or replaced. If it takes significantly less than N cycles to move the floater (76) from the top to the bottom position, it implies there is some kind of leakage which in the drainage path (40) or elsewhere. After N cycles also, if the floating device (75) is not coming down implies that either plunger (50) has jammed or solenoid coil (21) is inoperative, or extra water in fuel or floating device (75) is stuck or the lower magnetic switch (91) has failed; and which can be detected by measuring a width of the current pulse with respect to the pulse width modulated voltage wave. In the event of a vehicle having run for say more than 20000 km or so as per the vessel (1) volume and there is no instance of detection of the floating device (75) on the top position then it can be indication of something going wrong with magnet or failed upper magnetic switch (89) or water ingress in floating device (75). Also, if the floating device (75) comes in the vicinity of the lower magnetic switch (91) much before N cycles implies the upper magnetic switch (89) has failed, else the floating device (75) getting stuck in the path else a magnetization or a dislocation of the permanent magnet (88). If the lower magnetic switch (91) fails then the floating device (75) will come down and close the path to the inlet non-return valve (33) and thus pump will stop moving or move very sluggish and that can give indication that floating device (75) has blocked the inlet non-return valve (33) but still the lower position is not getting detected.

A plurality of error codes are generated decoding a variation of an actual number of cycles Na with reference to the calibrated cycles N. Illustratively: Error Code 01 may imply "Internal Leakage" if Na is substantially less than N. These error codes may be communicated to the ECU (90) for display and counteraction.

No air or dust or contamination of any kind from atmosphere is able to enter the holding chamber (122) due to a two non-return valves installed (35 & 33) and the sealing surface (23) of the sealing seat (27) having tight shut off with the orifice (134).

As an embodiment, the upper magnetic switch (89) and the plurality of bare probes (61) are connected in parallel so that the Electronic Control Unit (90) can allow the solenoid coil (21) to be energized when either of the signals is available. In case the signals are not consistent with each other in such case the Electronic Control Unit (90) can generate an error code and process the signal (energize or not energize the solenoid coil (21)) as calibrated.

As another embodiment, the upper magnetic switch (89) and the plurality of bare probes (61) are connected in series so that the solenoid coil (21) energizes only when both the signals are available.

As the sealing seat (27) plugs the orifice (134) under a force of the compression spring (29), the plunger (50) will not move under vibration till a value of [mass of plunger (50)×vibration acceleration] due to vibration is less than the force due to the compression spring (29).

Also, the sealing seat (27) will not recede and therefore not unblock the orifice (134), in case due to any reason a positive pressure is formed in the holding chamber (122) area (Majorly due to mechanical shocks), as the sealing seat (27) is pushed up by the force of the compression spring (29). Thus need of having higher cracking pressure of the outlet non-return valve (35) is eliminated.

The spherical end (77) and the "First fluid" spherical end (77) of the floating device (75) are same.

Dotted line(s) on one or more side in drawings signify that only a partial view is being shown.

I claim:

1. A solenoid operated unit (100) for detecting and removing with diagnostic metering an undesired fluid (6) from a desired fluid (5) of lower specific gravity than that of the undesired fluid (6), the solenoid operated unit (100) comprising:
   a unified solenoid operated pump and valve unit (70) comprising,
      a combination housing (110) having a first housing (120) and a second housing (140),
      a solenoid coil circuit (10) having an electromagnetic circuit integrated with a fluid circuit, and
      a pump-valve assembly (20) further comprising a unified chamber (26) having a first liner (222) and a second liner (223), a plunger (50), a receiver (160), an air reliever (180) and a sealing seat (27);
   a drainage path of the undesired fluid (40) between a holding chamber (122) and a drainage chamber (124) and comprising,
      an inlet non-return valve (33) disposed at a first mounting provision (125) in the first housing (120), and
      an outlet non-return valve (35) disposed at a second mounting provision (126) of the first housing (120);
   an electrical detection system (60);
   a mecha-electro-magnetic detection system (80); and
   a junction box (190) interacting with an electronic control unit (90) comprising a pulse width modulated (PWM) wave generator,
   the first housing (120) having a provision to dispose thereon a modular float chamber (127) having a floating device (75) comprising a "First Fluid" spherical end (77) and a "Second Fluid" spherical end (77A), the first housing (120) mounted on the second housing (140) on a mating surface (141) of the second housing (140) such that a first junction chamber (129) of the first housing (120) orients with a second junction chamber (142) of the second housing (140) and forms the junction box (190) and a common axis (130) of the first housing (120) and the second housing (140) becomes co-axial, consequently a first cylindrical chamber (131) of the first housing (120) and a second cylindrical chamber (132) of the second housing (140) forms the unified chamber (26), the first housing (120) comprising to the drainage path (40) of the undesired fluid (6), the electrical detection system (60), the mecha-electromagnetic detection system (80), the second housing (140) comprising to the electromagnetic circuit, the pump-valve assembly (20) accommodated partially in the first housing (120) and partially in the second housing (140), the solenoid operated unit (100) mounted at the bottom of a vessel (1), wherein the plunger (50) moves from up to down, a sweeping volume (28) with a cycle of a PWM electricity wave, while moving down the plunger (50) creates a negative pressure in the sweeping volume (28) and while moving up a positive pressure gets created in the sweeping volume (28), the air reliever (180) is provided for breathing, the solenoid operated unit (100) senses a real-time position of the floating device (75), has a calibrated number of cycles N of the PWM electricity wave for the diagnostic metering, an error list decodes a variation of an actual number of cycles Na with reference to the calibrated number of cycles N of the PWM electricity wave.

2. The solenoid operated unit (100) as claimed in claim 1, wherein the floating device (75) has the "First Fluid" spherical end (77) facing the drainage path (40) when deployed for a desirable first fluid.

3. The solenoid operated unit (100) as claimed in claim 1, wherein the floating device (75) has the "Second Fluid" spherical end (77A) facing the drainage path (40) when deployed for a desirable second fluid.

4. The solenoid operated unit (100) as claimed in claim 1, wherein the floating device (75) is unidirectionally disposed in the modular float chamber (127) slidably.

5. The solenoid operated unit (100) as claimed in claim 1, wherein the floating device (75) is molded from an engineering plastic material with a prescribed volume of an atmospheric air (86) entrapped.

6. The solenoid operated unit (100) as claimed in claim 1, wherein the first housing (120) comprises an interfacing surface (121), the holding chamber (122) having a bottom surface (123) and an orifice (134), the drainage chamber (124), the first mounting provision (125) and the second mounting provision (126).

7. The solenoid operated unit (100) as claimed in claim 1, wherein the first housing (120) further comprises an associated chamber (128) and the first junction chamber (129).

8. The solenoid operated unit (100) as claimed in claim 1, wherein the electromagnetic circuit involves a solenoid coil (21), a C-core, the plunger (50), the first liner (222), the second liner (223) and the receiver (160).

9. The solenoid operated unit (100) as claimed in claim 1, wherein the plunger (50) is made of a ferromagnetic material with low residual magnetism retention, has a large cylindrical surface (57) and a small cylindrical surface (58), a head (52) with a neck (51) on the small cylindrical surface (58) towards a suction end (53), a first room (49) and an external frustum (55) towards a spring end (54), a plurality of longitudinal grooves (56) is provided on the large cylindrical surface (57).

10. The solenoid operated unit (100) as claimed in claim 1, wherein the first liner (222) is a thin hollow cylinder made of a ferromagnetic, low frictional co-efficient metal or metal alloy, has a first liner inner surface (222A) and a first liner outer surface (222B).

11. The solenoid operated unit (100) as claimed in claim 1, wherein the second liner (223) is a thin hollow cylinder made of a nonmagnetic, low frictional co-efficient metal or metal alloy, has a second liner inner surface (223A) and a second liner outer surface (223B).

12. The solenoid operated unit (100) as claimed in claim 1, wherein the receiver (160) is made of a ferromagnetic material with low residual magnetism retention, has an internal frustum (161), a base (162), a peripheral seat (163) and a second room (164), and there is provided an airway (165).

13. The solenoid operated unit (100) as claimed in claim 1, wherein the air reliever (180) is a bidirectional membrane that lets an atmospheric air cross from an inside (181) to an outside (182) of the air reliever (180) depending on differential pressure on its two sides, the bidirectional membrane does not allow liquid and dust particles to cross from the outside (182) to the inside (181) of the air reliever (180).

14. The solenoid operated unit (100) as claimed in claim 1, wherein the sealing seat (27) is made of rubber, whether natural or synthetic, of durometer hardness more than 40, having a sealing surface (23) and a cavity (22) complementary in profile to a head (52) and a neck (51) of the plunger (50), the sealing seat (27) mounted on the plunger (50) by elastic deformation.

15. The solenoid operated unit (100) as claimed in claim 1, wherein the receiver (160) is rigidly disposed at a lower end of the second housing (140).

16. The solenoid operated unit (100) as claimed in claim 1, wherein the air reliever (180) is disposed in a second room (164) of the receiver (160).

17. The solenoid operated unit (100) as claimed in claim 1, wherein the second liner (223) sits on a peripheral seat (163) of the receiver (160) such that a second liner outer surface (223B) of the second liner (223) sits against a wall of the unified chamber (26), the first liner (222) sits adjacent to the second liner (223) such that the first liner outer surface (222B) of the first liner (222) sits against the wall of the unified chamber (26).

18. The solenoid operated unit (100) as claimed in claim 1, wherein the plunger (50) with the sealing seat (27) linearly moves glidingly on a first liner inner surface (222A) of the first liner (222) and a second liner inner surface (223A) of the second liner (223) under an influence of the magnetism and a compression spring (29).

19. The solenoid operated unit (100) as claimed in claim 1, wherein the plunger (50) can move up till a sealing surface (23) of the sealing seat (27) hits a bottom orifice (134) of the holding chamber (122), and can move down till a frustum base (59) of the plunger (50) hits a base (162) of the receiver (160).

20. The solenoid operated unit (100) as claimed in claim 1, wherein the sweeping volume (28) is a volume above a sealing surface (23) of the sealing seat (27) till a bottom surface (123) of the holding chamber (122).

21. The solenoid operated unit (100) as claimed in claim 1, wherein the sweeping volume (28) is fluidically insulated from a remaining close channel by a seal (36).

22. The solenoid operated unit (100) as claimed in claim 1, wherein the electrical detection system (60) encapsulatedly housed in an associated chamber (128) of the first housing (120) comprises a electrical circuitry assembly having a plurality of bare probes (61) placed at a predetermined distance between each other, which are connected to an electrical circuitry such that when the plurality of bare probes (61) have the desired fluid (5) around them, the output voltage is nearly equal to a source voltage Vs1 (106); which drops to about 50% value when the plurality of bare probes (61) have the undesired fluid (6) around them.

23. The solenoid operated unit (100) as claimed in claim 1, wherein the mecha-electro-magnetic detection system (80) comprises:
   the modular float chamber (127) disposed on the first housing (120),
   the floating device (75), and
   an electro-magnetic circuitry assembly (84) comprising an upper magnetic switch (89), a lower magnetic switch (91), a first resistance X (101), a second resistance Y (102), a third resistance A (103) and a fourth resistance Z (104).

24. The electro-magnetic circuitry assembly (84) as claimed in claim 23, wherein the electro-magnetic circuitry assembly (84) and an electrical circuit assembly are integrated to a unit circuitry assembly (85) and encapsulatedly housed in an associated chamber (128) of the first housing (120).

25. The solenoid operated unit (100) as claimed in claim 1, wherein the floating device (75) comprises a floater (76) and a permanent magnet (88), a mass and volume of the floating device (75) is such that the floating device (75) floats in the undesired fluid (6) and sinks in the desired fluid (5), the floating device (75) has the "First Fluid" spherical end (77) and the "Second Fluid" spherical end (77A) and a cylindrical part (78) in between, the floater (76) is symmetrical in shape about a longitudinal plane (79) containing a longitudinal axis (81) of the cylindrical part (78), the cylindrical part (78) has a plurality of longitudinal recess (83), the permanent magnet (88) is disposed on a surface (87) of the cylindrical part (78) asymmetrical about the radial plane (82) and oriented such a way that a magnet inside is in front of a magnet switch.

26. The solenoid operated unit (100) as claimed in claim 1, wherein the modular float chamber (127) has a plurality of longitudinal projections (92) complementary to a plurality of longitudinal recess (83) on a floater (76) of the floating device (75), constraining any random movement of the floater (76) except along a longitudinal axis (81).

27. The solenoid operated unit (100) as claimed in claim 1, wherein the mecha-electro-magnetic detection system (80) and the electrical detection system (60) send an output to the electronic control unit (90) which energizes a solenoid coil (21) when the detection systems (60 and 80) sense the undesired fluid (6).

28. The solenoid operated unit (100) as claimed in claim 1, wherein the solenoid operated unit (100) is mounted at the bottom of the vessel (1) through an interfacing surface (121) of the first housing (120), with the fluid (5,6) in the vessel (1), a plurality of bare probes (61) of the electrical detection system (60) and the floating device (75) of the mecha-electro-magnetic detection system (80) project up and are surrounded by the fluid (5,6), when the plurality of bare probes (61) are surrounded by the desired fluid (5), the "First fluid" spherical end (77) of the floating device (75) sits and seals an inlet opening (33A), of the inlet non-return valve (33).

29. The solenoid operated unit (100) as claimed in claim 28, wherein the floating device (75) lifts up when the undesired fluid (6) is adequate to surround the plurality of bare probes (61) and/or lift up the floating device (75) so that a permanent magnet (88) is in front of an upper magnetic switch (89), then a solenoid coil (21) is energized and the plunger (50) starts moving to and fro creating negative pressure and positive pressure alternately, when negative pressure is created, the undesired fluid (6) of a volume equal to that of the sweeping volume (28) is drawn into the drainage path (40), when positive pressure is created, the undesired fluid (6) pushes open the outlet non-return valve (35) and exits the drainage path (40), the solenoid operated unit (100) not depending on a fluid column pressure for bleeding of the undesired fluid (6).

30. The solenoid operated unit (100) as claimed in claim 1, wherein the electrical detection system (60) and the mecha-electro-magnetic detection system (80) are connected in parallel.

31. The solenoid operated unit (100) as claimed in claim 1, wherein the electrical detection system (60) and the mecha-electro-magnetic detection system (80) are connected in series.

32. The solenoid operated unit (100) as claimed in claim 1, wherein the sealing seat (27) plugs an orifice (134) under a force of a compression spring (29) and the plunger (50) does not move down under a vibration till a value of the mass of plunger (50)×a vibration acceleration due to the vibration is less than the force due of the compression spring (29).

33. The solenoid operated unit (100) as claimed in claim 1, wherein the sealing seat (27) does not recede and does not unblock an orifice (134) when a positive pressure is formed in the holding chamber (122) area as the sealing seat (27) is pushed up by a force of a compression spring (29).

* * * * *